US008696666B2

(12) United States Patent
Sanai et al.

(10) Patent No.: US 8,696,666 B2
(45) Date of Patent: Apr. 15, 2014

(54) MEDICAL APPARATUS AND SURGICAL TREATMENT INSTRUMENT

(75) Inventors: Hideo Sanai, Hachioji (JP); Ryu Onuma, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 365 days.

(21) Appl. No.: 13/084,643

(22) Filed: Apr. 12, 2011

(65) Prior Publication Data

US 2011/0288451 A1   Nov. 24, 2011

Related U.S. Application Data

(63) Continuation of application No. PCT/JP2010/068195, filed on Oct. 15, 2010.

(60) Provisional application No. 61/319,386, filed on Mar. 31, 2010.

(51) Int. Cl.
*A61B 18/18* (2006.01)
(52) U.S. Cl.
USPC .................. 606/51; 606/40; 606/41; 606/169
(58) Field of Classification Search
USPC ...................................... 606/50–52, 167–169
See application file for complete search history.

(56) References Cited

U.S. PATENT DOCUMENTS

| | | | |
|---|---|---|---|
| 5,628,760 | A | 5/1997 | Knoepfler |
| 2006/0234222 | A1 | 10/2006 | McKeown et al. |
| 2006/0241532 | A1 | 10/2006 | Murakami |
| 2008/0293008 | A1 | 11/2008 | Regere et al. |
| 2009/0248050 | A1 | 10/2009 | Hirai |

FOREIGN PATENT DOCUMENTS

| | | |
|---|---|---|
| EP | 1 731 110 A1 | 12/2006 |
| EP | 2 105 099 A1 | 9/2009 |
| JP | 2003-210480 | 7/2003 |
| JP | 2003-210480 A | 7/2003 |
| JP | 2005-6722 A | 1/2005 |
| JP | 2005-278933 | 10/2005 |
| JP | 2008-036390 | 2/2008 |
| JP | 2008-272393 | 11/2008 |
| JP | 2009-078155 | 4/2009 |

(Continued)

OTHER PUBLICATIONS

European Search Report dated Oct. 24, 2012 from corresponding Patent Application No. EP 10 84 9000.4.

(Continued)

*Primary Examiner* — Linda Dvorak
*Assistant Examiner* — Jaymi Della
(74) *Attorney, Agent, or Firm* — Scully, Scott, Murphy & Presser, P.C.

(57) ABSTRACT

A medical apparatus includes: a main body apparatus switchable to a mode for outputting ultrasound vibration, mode for outputting high-frequency current, and mode for simultaneously outputting the ultrasound vibration and the high-frequency current; a probe for performing a first treatment with a first treatment portion; a first attaching and detaching portion including a first electric armature; an insertion portion including a second treatment portion, and configured to perform a second treatment, with a living tissue held between the first treatment portion and the second treatment portion; a second attaching and detaching portion including a second electric armature; a switch control section which switches the output of the high-frequency current to a monopolar output or a bipolar output according to a connection state between the first electric armature and the second electric armature.

10 Claims, 17 Drawing Sheets

(56) References Cited

FOREIGN PATENT DOCUMENTS

| JP | 2009-526554 | 7/2009 |
| JP | 2009-233329 | 10/2009 |
| WO | WO 03/059945 A2 | 7/2003 |

OTHER PUBLICATIONS

Abstract of International Publication No. WO 2007/149595 A2, dated Dec. 27, 2007.

MEDICAL APPARATUS AND SURGICAL TREATMENT INSTRUMENT

CROSS REFERENCE TO RELATED APPLICATION

This application is a continuation application of PCT/JP2010/068195 filed on Oct. 15, 2010 and claims benefit of U.S. Provisional Patent Application No. 61/319,386 filed in the U.S.A. on Mar. 31, 2010, the entire contents of which are incorporated herein by this reference.

BACKGROUND OF THE INVENTION

1. Field of the Invention

The present invention relates to a medical apparatus and a surgical treatment instrument, and particularly relates to a medical apparatus and a surgical treatment instrument which can output at least one of an ultrasound vibration and a high-frequency current.

2. Description of the Related Art

Surgical treatment instruments are used for performing treatment such as dissection and coagulation of living tissue in surgical operations. There are types of surgical treatment instruments in accordance with the shapes of the treatment portions, such as the type for performing treatment by holding living tissue (a so-called scissors-shaped type), and the type for performing treatment by being brought into contact with living tissue (for example, a hook-shaped or a spatulate type). Further, in surgical treatment instruments, for example, an ultrasound treatment instrument capable of outputting ultrasound, and a high-frequency treatment instrument capable of outputting a high-frequency current are known.

For example, in a scissors-shaped type ultrasound treatment instrument, one member makes ultrasound vibration, whereas the other jaw member is opened and closed with respect to the one member for holding. In a spatulate type ultrasound treatment instrument, one probe with a distal end formed into a spatulate shape makes ultrasound vibration. Further, in a scissors-shaped type high-frequency treatment instrument, bipolar output of a high-frequency current is performed with use of two members, whereas in a spatulate type high-frequency treatment instrument, monopolar output is performed with use of one probe with a distal end formed into a spatulate shape and a counter electrode plate.

Furthermore, Japanese Patent Application Laid-Open Publication No. 2009-78155 proposes forceps capable of both bipolar output and monopolar output in a high-frequency treatment instrument.

Incidentally, on the occasion of a surgical operation, a surgeon selects a treatment instrument suitable for treatment to perform the treatment. During a surgical operation, the treatment instrument suitable for treatment is often changed. Change of the treatment instrument is, for example, under observation of laparoscope, change to a spatulate ultrasound treatment instrument from a scissors-shaped ultrasound treatment instrument, or change to a spatulate high-frequency treatment instrument from a scissors-shaped high-frequency treatment instrument.

When a surgeon has different treatment instruments respectively in his left and right hands, for change of a treatment instrument, more often than not, the surgeon instructs a nurse or the like about the change, hands the treatment instrument which the surgeon has used, for example, a scissors-shaped ultrasound treatment instrument, to the nurse or the like, and receives the treatment instrument to be used next, for example, a spatulate ultrasound treatment instrument, from the nurse or the like.

At this time, the nurse or the like removes the handed treatment instrument from the corresponding control apparatus, connects the treatment instrument to be used next by the surgeon to the corresponding control apparatus to set the treatment instrument into a usable state, and thereafter, hands the treatment instrument to the surgeon.

Further, the high-frequency treatment instrument proposed in the above described Japanese Patent Application Laid-Open Publication No. 2009-78155 is forceps which has the structure in which the extended portion of the monopolar element is provided at the distal end portion of one of the two members of the bipolar forceps. According to the high-frequency treatment instrument, the monopolar treatment instrument and the bipolar treatment instrument do not have to be individually prepared, and a surgeon can perform treatment by monopolar output and bipolar output with one treatment instrument.

SUMMARY OF THE INVENTION

A medical apparatus of one mode of the present invention includes a first device including a grasping portion grasped by a surgeon, a probe connected to the grasping portion and capable of transmitting at least one of an ultrasound vibration and a high-frequency current, and a first treatment portion which is provided at a distal end portion of the probe and is for transmitting at least one of the ultrasound vibration and the high-frequency current transmitted by the probe to living tissue, a cable which is connected to the first device and is for supplying at least one of an ultrasound vibration and a high-frequency current to the first device, a main body apparatus which is connected to the cable and is capable of outputting a drive signal for driving at least one of the ultrasound vibration and the high-frequency current, a second device including a second treatment portion for holding living tissue between the first treatment portion and the second treatment portion, a movable handle for holding the living tissue by moving the second treatment portion toward the first treatment portion, and an attaching and detaching portion for being attachably and detachably engaged with the first device to which the cable is connected, and a connection signal output portion for outputting a connection signal indicating that the first device is connected to the attaching and detaching portion of the second device, wherein the main body apparatus has a switch control section which detects that the second device is fitted to the first device based on the connection signal from the connection signal output portion, and switches an output condition of the drive signal in the main body apparatus.

A surgical treatment instrument of one mode of the present invention is a surgical treatment instrument having a grasping portion grasped by a surgeon, a probe which is connected to the grasping portion and is capable of transmitting at least one of an ultrasound vibration and a high-frequency current, a first treatment portion which is provided at a distal end portion of the probe and is for transmitting at least one of the ultrasound vibration and the high-frequency current which the probe transmits, to living tissue, and a cable which is connected to the first device and is for supplying treatment energy including at least one of an ultrasound vibration and a high-frequency current to the first device, and has a connection signal output portion capable of outputting a connection signal indicating connection of a device having a second treatment portion located at a position opposed to a distal end portion of the probe when fitted to the surgical treatment instrument to which the cable is connected.

BRIEF DESCRIPTION OF THE DRAWINGS

FIG. 12 is a front view of a receptacle 161 in a connector portion 3a;

DETAILED DESCRIPTION OF THE PREFERRED EMBODIMENT(S)

(Entire Configuration)

Figure 1:
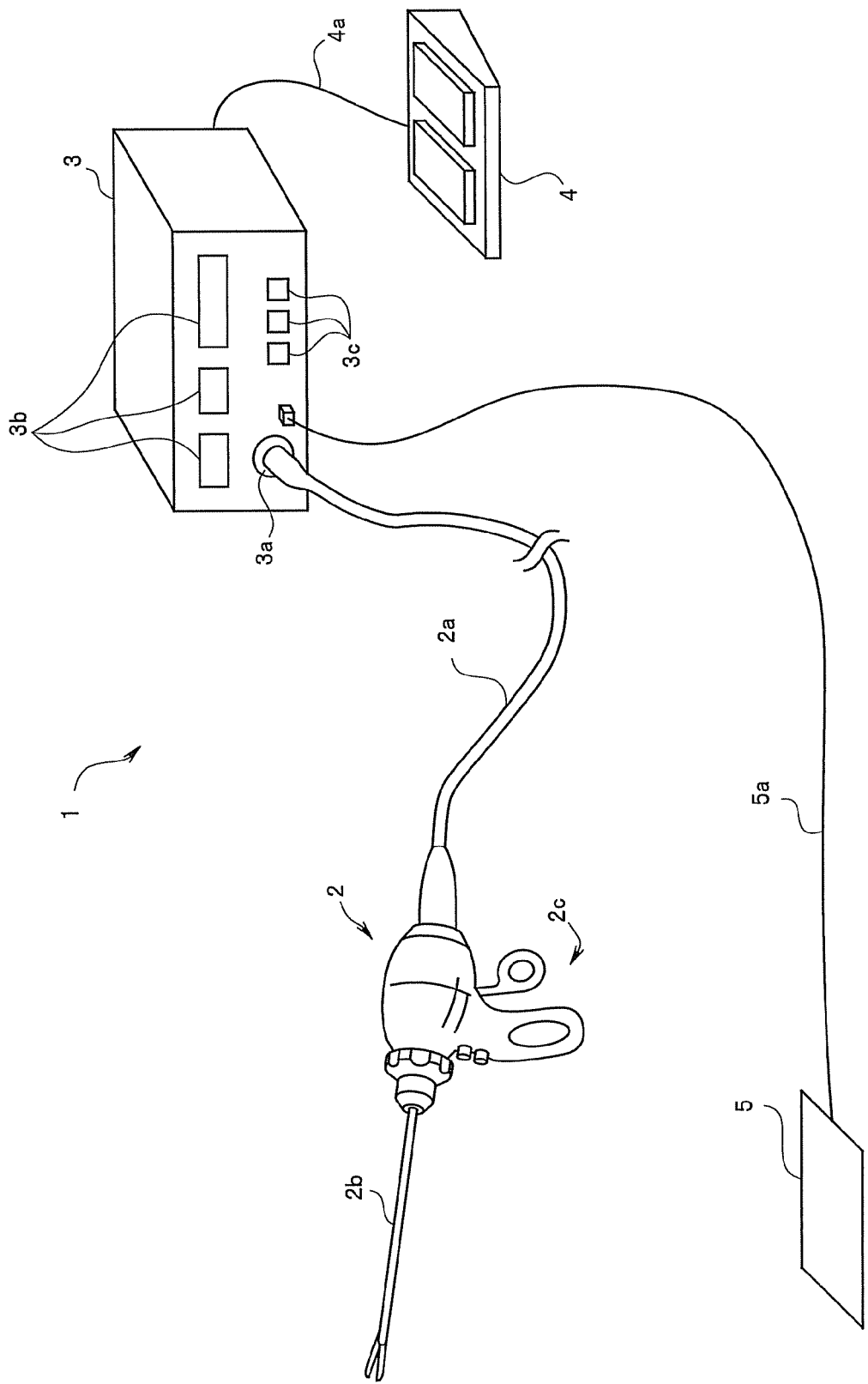
FIG. 1 is a view showing a configuration of a surgical operation system according to an embodiment of the present invention.

FIG. 1 is a view showing a configuration of a surgical operation system according to an embodiment of the present invention. A surgical operation system 1 which is a medical apparatus is configured by including a handpiece 2, a main body apparatus 3 which is an output control apparatus, a foot switch 4 and a counter electrode plate 5.

The handpiece 2 is a surgical treatment instrument capable of both ultrasound output and high-frequency current output. The handpiece 2 is connected to the main body apparatus 3 via a cable 2a which is attachable and detachable. The handpiece 2 has an insertion portion 2b and a handle portion 2c.

The main body apparatus 3 as a control unit supplies at least one of a drive signal for outputting ultrasound and a drive signal for outputting a high-frequency current in accordance with setting. More specifically, the main body apparatus 3 has three output modes, that is, an ultrasound output mode, a high-frequency output mode, and a simultaneous output mode of ultrasound and high frequency. The output mode is set by various operation buttons 3c and the like provided at the main body apparatus 3. Further, the main body apparatus 3 contains a speaker (not illustrated) for outputting a sound or a voice.

The main body apparatus 3 has a plurality of displays 3b and a plurality of various operation buttons 3c. The display 3b displays a set value or the like, and various operation buttons 3c are buttons for performing setting or the like of various outputs.

The foot switch 4 is connected to the main body apparatus 3 through a cable 4a, and when a surgeon presses the foot switch 4 by foot, the foot switch 4 outputs a predetermined operation signal FS, and supplies the operation signal FS to the main body apparatus 3. The foot switch 4 is a switch for turning on or off ultrasound output at the time of the ultrasound output, and is a switch for turning on or off high-frequency output at the time of the high-frequency output. Setting of the output values of an ultrasound vibration and a high-frequency current is performed by operation of the operation button of an operation panel of the main body apparatus 3.

The counter electrode plate 5 is connected to the main body apparatus 3 through a cable 5a. The counter electrode plate 5 is a return electrode for returning a current which passes through a subject at the time of monopolar output of a high-frequency current.

A surgeon can perform a surgical operation under observation of laparoscope with the handpiece 2 in one hand and another treatment instrument in the other hand.

(Configuration of Handpiece)

Figure 2:
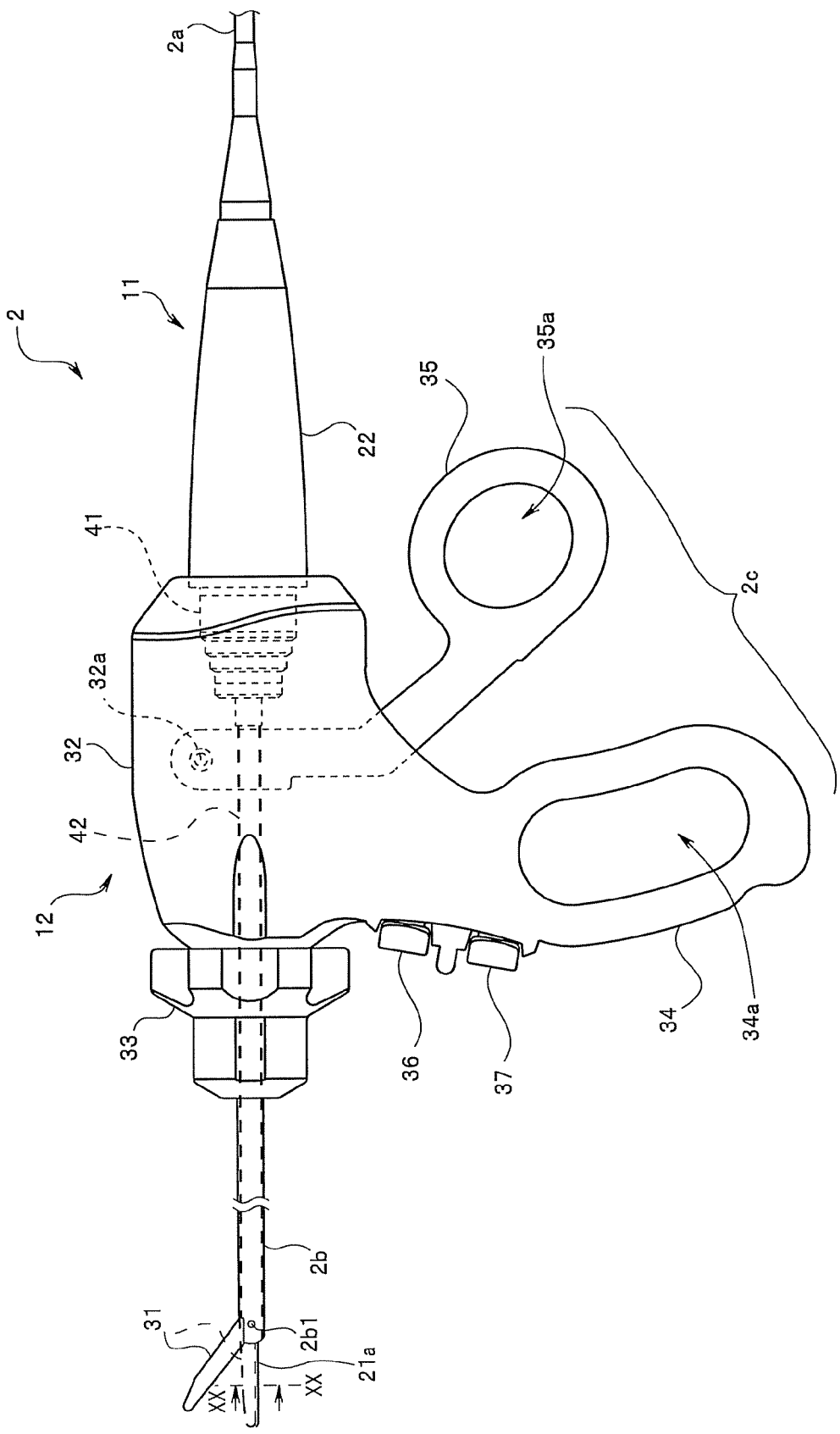
FIG. 2 is a front view showing a configuration of a handpiece 2 according to the present invention.
Figure 3:
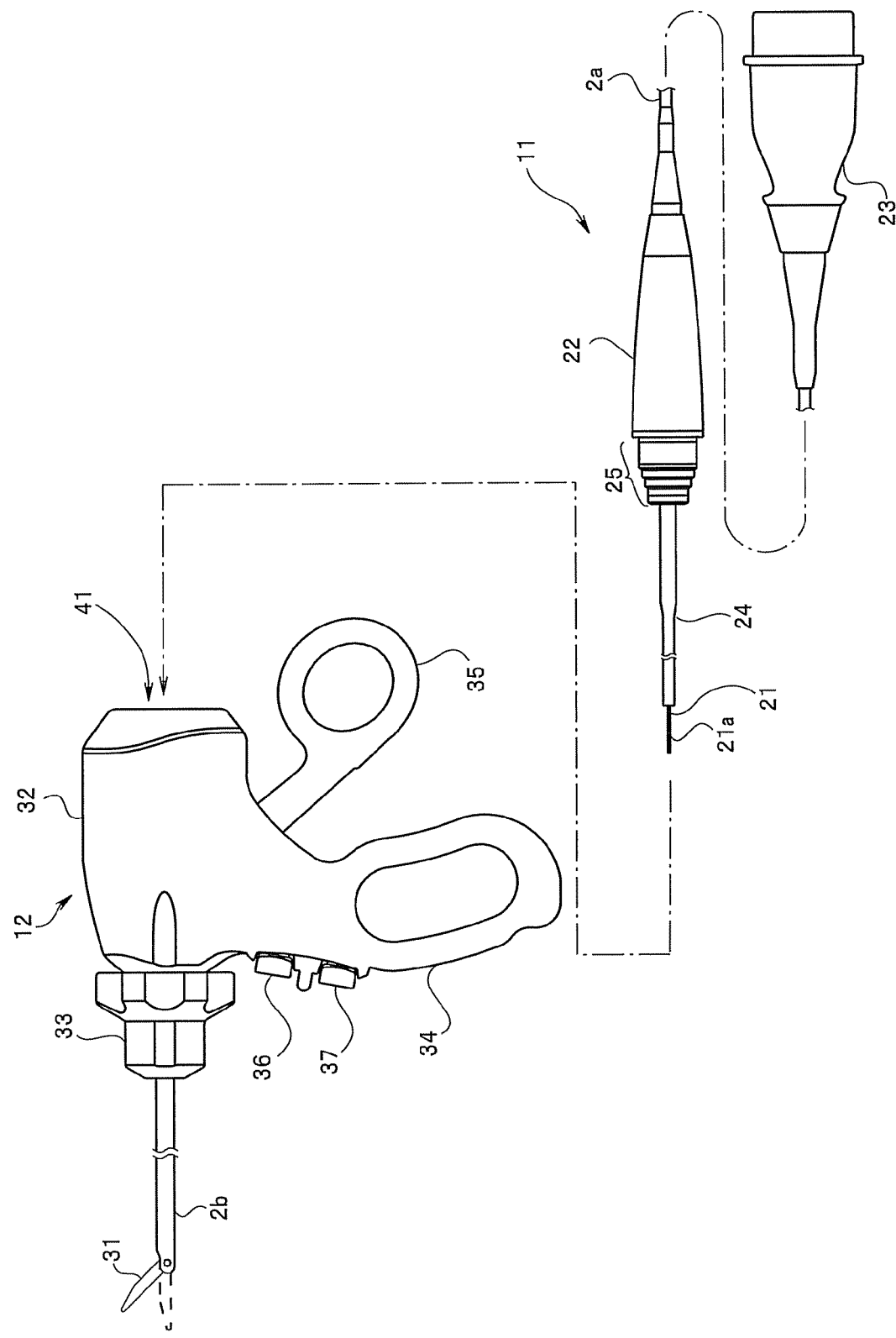
FIG. 3 is a view showing a state in which two devices configuring the handpiece 2, that is, a first device 11 and a second device 12 are separated.

FIGS. 2 and 3 are views showing a configuration of the handpiece 2 according to the present embodiment. FIG. 2 is a front view showing the configuration of the handpiece 2 according to the present embodiment. FIG. 3 is a view showing a state in which two devices which configure the handpiece 2, that is, a first device 11 and a second device 12 are separated. As shown in FIG. 3, the handpiece 2 is configured by the first device 11 being fitted in the second device 12.

As shown in FIG. 3, the first device 11 is a surgical treatment instrument having a probe 21 capable of transmitting an ultrasound vibration, a substantially columnar grasping portion 22 provided at a proximal end side of the probe 21, the cable 2a provided at a proximal end side of the grasping portion 22, and a connector portion 23 provided at a proximal end portion of the cable 2a.

The probe 21 is a conductive shaft member which is connected to the grasping portion 22 and is capable of transmitting at least one of an ultrasound vibration and a high-frequency current. A distal end portion of the probe 21 is a treatment portion 21a having a spatulate shape. The treatment portion 21a is a portion which is provided at the distal end portion of the probe 21 and is for transmitting at least one of the ultrasound vibration and the high-frequency current transmitted by the probe to living tissue. An insulating sheath 24 is provided so that an outer peripheral portion of the probe 21 is covered with the insulating sheath 24 from a distal end portion of the grasping portion 22 to the vicinity of the distal end portion of the probe 21. However, the distal end portion of the probe 21 is protruded from a distal end opening of the insulating sheath 24. More specifically, a portion other than the treatment portion 21a of the distal end portion of the probe 21 is covered with the insulating sheath 24. The connector portion 23 is configured to be attachable to and detachable from a connector portion 3a of the main body apparatus 3. When the connector portion 23 is connected to the connector portion 3a, a plug in the connector portion 23 is engaged with a receptacle of the connector portion 3a. A configuration of the plug and the receptacle will be described later.

The first device 11 has a stepped portion 25 provided with a plurality of electric armatures, between the grasping portion 22 and the insulating sheath 24. The stepped portion 25 includes a plurality of columnar stepped portions which are formed so that diameters become smaller stepwise from the grasping portion 22 toward the distal end of the insulating sheath 24. The stepped portion 25 is in a shape capable of being engaged with a recessed portion 41 of the second device so that the first device 11 can be fitted in the second device 12. Accordingly, the recessed portion 41 of the second device 12 is provided with a plurality of stepped portions in an inner peripheral portion so that the stepped portion 25 is engaged with the stepped portions. More specifically, the recessed portion 41 configures an attaching and detaching portion for the second device 12 to be attachably and detachably engaged with the first device 11.

Further, as will be described later, the first device 11 is also a surgical treatment instrument, that is, a handpiece capable of ultrasound output, high-frequency output, and simultaneous output of ultrasound and high frequency, by itself. More detailed configuration of the first device 11 will be described later.

The second device 12 has the insertion portion 2b provided with a movable jaw 31 at a distal end portion, an operation portion main body 32 provided at a proximal end side of the insertion portion 2b, and the handle portion 2c provided at the operation portion main body 32.

The insertion portion 2b is a tubular member made of a conductive material with an outer peripheral surface covered with an insulating layer, and has the movable jaw 31 at a distal end portion, which is pivotally supported by a pin 2b1, and is supported to be rotatable around the pin 2b1. A rear end of the movable jaw 31 is connected to a drive shaft (not illustrated). As will be described later, the movable jaw 31 is openable and closable in a vertical direction in FIGS. 2 and 3, through a drive shaft thereof (not illustrated) in response to an operation of the handle portion 2c.

At a proximal end portion of the insertion portion 2b, a rotation knob 33 for rotating the insertion portion 2b around an axis thereof is provided. The rotation knob 33 is fixed to an outer periphery of the proximal end portion of the insertion portion 2b. Meanwhile, the rotation knob 33 is not fixed to the operation portion main body 32, but is rotatably connected thereto. Accordingly, the rotation knob 33 is rotated, and thereby, the rotation knob 33 and the insertion portion 2b can be rotated around the longitudinal axis of the insertion portion 2b, with respect to the operation portion main body 32. A surgeon rotates the rotation knob 33 around the axis of the insertion portion 2b, and can set an opening and closing directions of the movable jaw 31 at an arbitrary direction.

The handle portion 2c includes a fixed handle 34 and a movable handle 35. The fixed handle 34 is formed integrally with the operation portion main body 32, and has a finger rest hole 34a in which a plurality of fingers except for a thumb of a surgeon is rested. The movable handle 35 is pivotally supported rotatably around a pin 32a provided at the operation portion main body 32. The movable handle 35 has a finger rest hole 35a at which the thumb of a surgeon is rested.

A proximal end portion of a drive shaft (not illustrated) connected to a rear end of the movable jaw 31 is connected to a spot in the vicinity of the pin 32a of the movable handle 35. The second device 12 is configured so that the movable jaw 31 is closed when the movable handle 35 is moved close to the fixed handle 34. More specifically, movement of the movable handle 35 with the pin 32a as the center of rotation is converted into movement of the movable jaw 31 with the support pin 2b1 as the center of rotation. In FIG. 2, a closed state of the movable jaw 31 is shown by a dotted line, whereas an opened state thereof is shown by a solid line.

More specifically, the movable jaw 31 is a treatment portion for holding living tissue between the treatment portion 21a and the movable jaw 31, and the movable handle 35 is an operation portion for holding living tissue by moving the movable jaw 31 which is the treatment portion toward the treatment portion 21a.

Further, the operation portion main body 32 is provided with two switch buttons 36 and 37. The switch button 36 is a switch for switching on and off ultrasound output or high-frequency current output. The switch 37 is a switch for changing the output value of ultrasound or high frequency. Operation signals HS of the switch buttons 36 and 37 of the operation portion main body 32 are supplied to the main body apparatus 3 through corresponding armatures 201b and 117b, a conductive member 188 and a signal line 2ab.

The switch buttons 36 and 37 may be allowed to function as the switches for only high-frequency output, and ultrasound output may be performed with only the foot switch 4.

Furthermore, on and off of ultrasound output or high-frequency current output and the output value may be changed not only by the two switches of the operation portion main body 32, but also by the various switches 3c of the main body apparatus 3. Setting of the output mode and the like may be performed not only by the various switches 3c of the main body apparatus 3, but also by the two switches of the operation portion main body 32.

At a proximal end side of the operation portion main body 32 of the second device 12, the recessed portion 41 as the attaching and detaching portion for attachably and detachably engaging the first device 11 is formed. The second device 12 has an insertion channel 42 where the insulating sheath 24 can be inserted after the distal end of the probe 21 of the first device 11 is inserted from the recessed portion 41. The recessed portion 41 is formed so that the stepped portion 25 of the first device 11 is engaged therewith. When the first device 11 is fitted in the second device 12 so that the stepped portion 25 is engaged with the recessed portion 41, the first device 11 and the second device 12 are connected, and the treatment portion 21a at the distal end portion of the probe 21 of the first device 11 is protruded from the insertion portion 2b of the second device 12 so as to be able to perform a holding operation with the movable jaw 31 of the second device. When the first device 11 and the second device 12 are connected, a treatment portion capable of holding living tissue by the distal end portion of the probe 21 and the movable jaw 31 is formed, and a plurality of electric armatures provided at the stepped portion 25 and a plurality of electric armatures provided at the recessed portion 41 are electrically connected with the armatures corresponding to each other being in contact with each other. The electrical connection will be described later.

Accordingly, during a surgical operation, a surgeon fits the second device 12 to the first device 11, and after treatment using the scissors-shaped handpiece 2, the surgeon pulls out the handpiece 2 from a trocar provided at a body wall of a subject. The surgeon removes the second device 12 from the first device 11, inserts the first device 11 into the trocar, and subsequently can perform treatment using the first device 11 in a spatulate shape as the handpiece. Further, on the contrary, after the treatment using the first device 11 in the spatulate shape, the surgeon pulls out the first device 11 from the trocar provided at the body wall of the subject to fit the second device 12 thereto, inserts the first device 11 with the second device 12 fitted thereto into the trocar, and subsequently can perform the treatment using the scissors-shaped handpiece 2.

At this time, as will be described later, it is detected in the main body apparatus 3 by a connection signal DS from the first device 11 that the second device 12 is fitted to the first device.

Accordingly, based on the detection result, the main body apparatus 3 outputs bipolar output when the connected treatment instrument is used, for example, as a scissors-shaped high-frequency treatment instrument, and outputs monopolar output when the connected treatment instrument is used as a spatulate high-frequency treatment instrument. Further, the main body apparatus 3 changes the output value in the case of the scissors-shaped ultrasound treatment instrument and in the case of the spatulate ultrasound treatment instrument, based on the detection result.

(First Device)

A configuration of the first device 11 will be described in detail.

Figure 4:
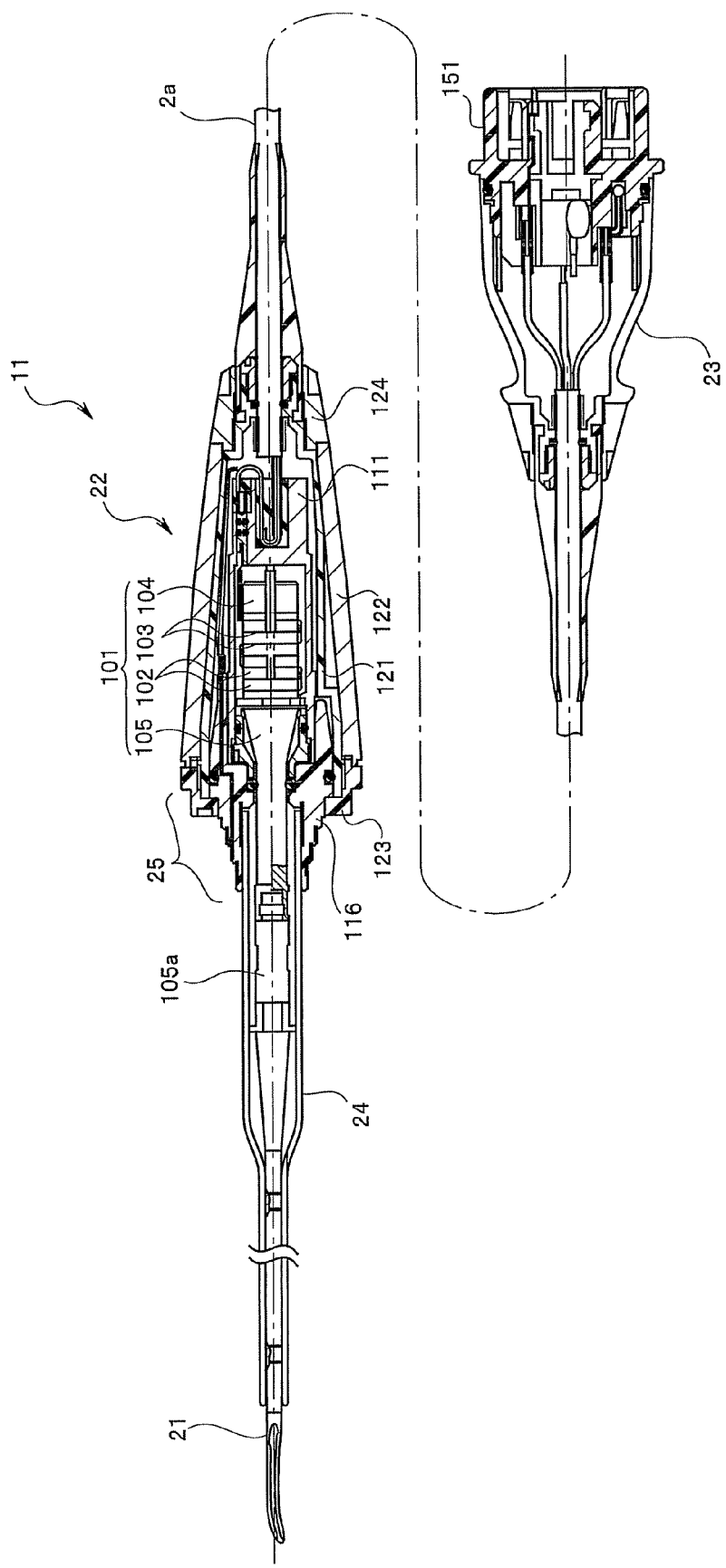
FIG. 4 is a sectional view of the first device 11.
Figure 5:
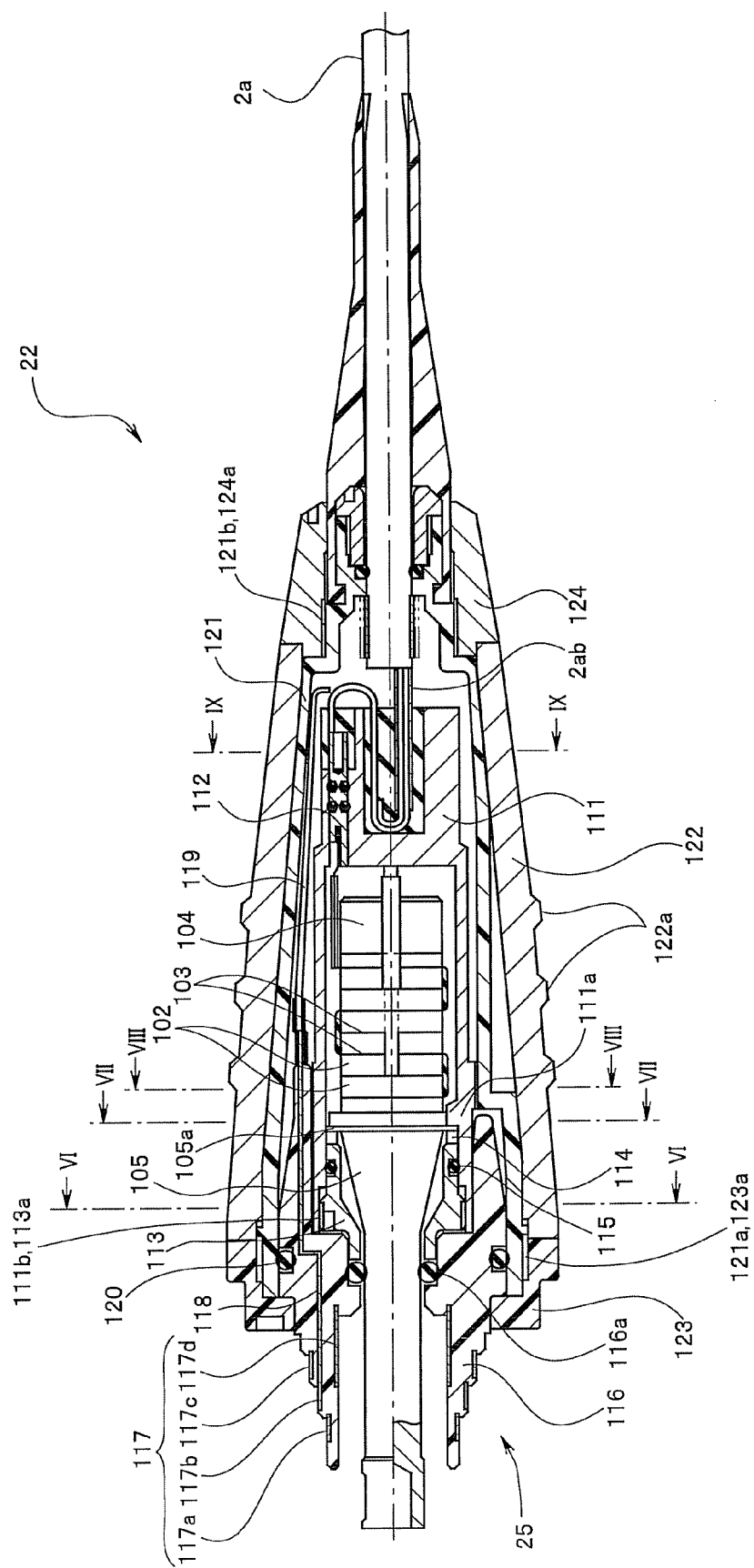
FIG. 5 is a sectional view of a grasping portion 22 of the first device 11.
Figure 6:
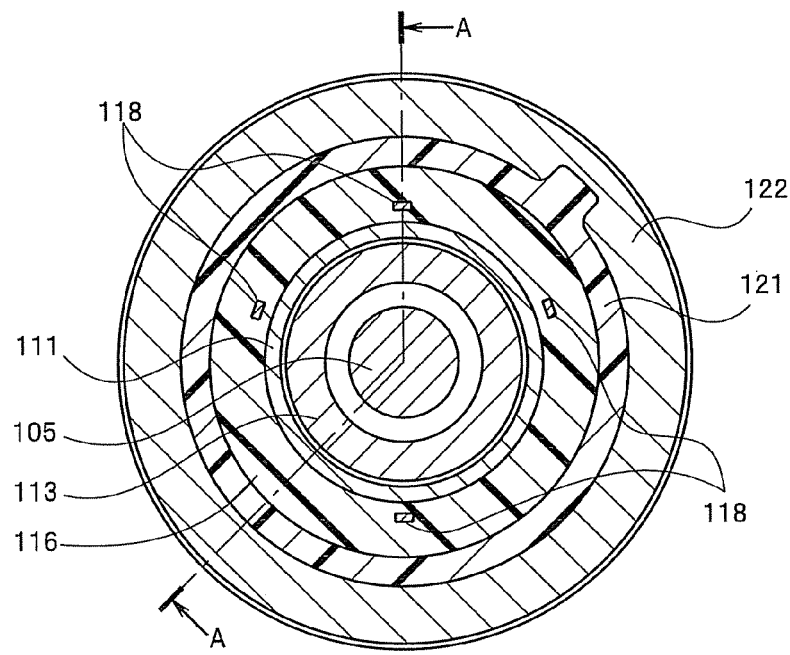
FIG. 6 is a sectional view taken along a VI-VI line of FIG. 5.
Figure 7:
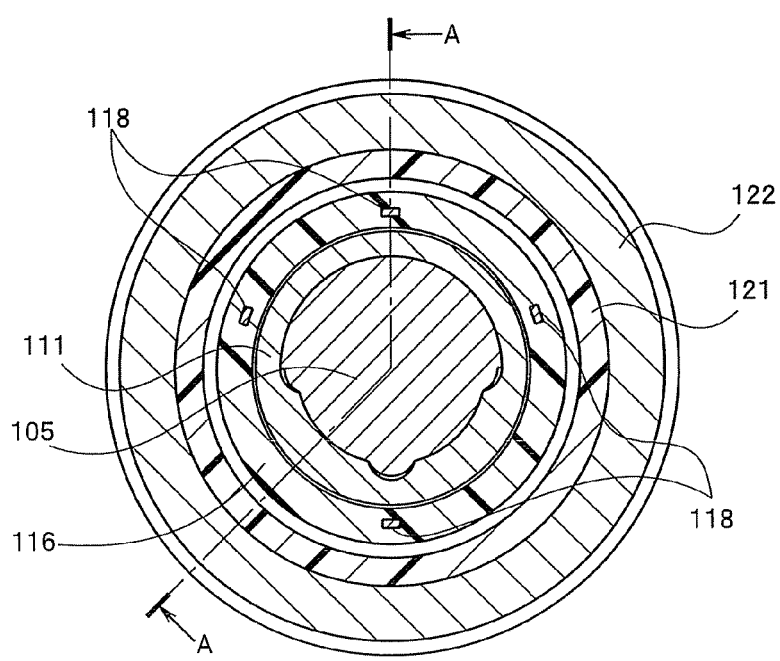
FIG. 7 is a sectional view taken along a VII-VII line of FIG. 5.
Figure 8:
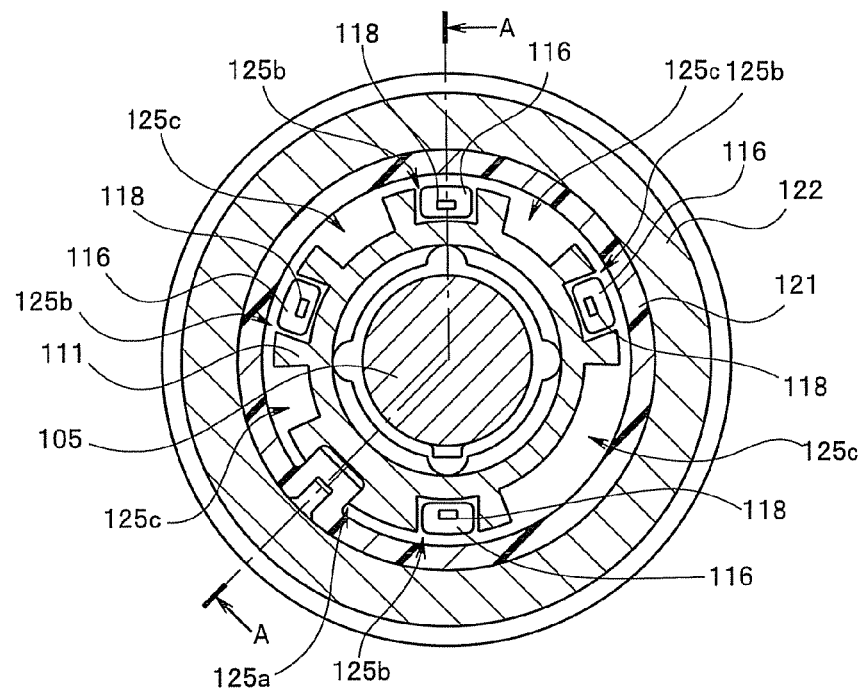
FIG. 8 is a sectional view taken along a VIII-VIII line of FIG. 5.
Figure 9:
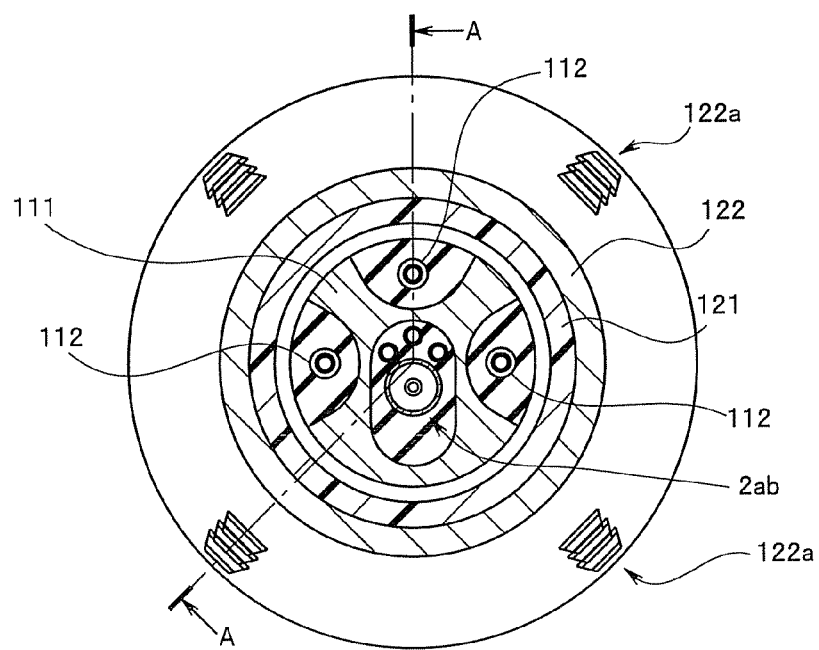
FIG. 9 is a sectional view taken along a IX-IX line of FIG. 5.

FIG. 4 is a sectional view of the first device 11. FIG. 4 is a sectional view seen from a top surface to show that the distal end portion of the probe 21 is spatulate. FIG. 5 is a sectional view of the grasping portion 22 of the first device 11. The treatment portion 21a at the distal end portion of the probe 21 is substantially straight in FIGS. 2 and 3, but since FIG. 4 is a sectional view seen from the top surface, the distal end portion is curved into a spatulate shape in FIG. 4. FIGS. 6 to 9 are sectional views of the grasping portion 22. FIGS. 4 and 5 are sectional views taken along A-A lines of FIGS. 6 to 9. FIG. 6 is a sectional view taken along a VI-VI line of FIG. 5. FIG. 7 is a sectional view taken along a VII-VII line of FIG. 5. FIG. 8 is a sectional view taken along a VIII-VIII line of FIG. 5. FIG. 9 is a sectional view taken along a IX-IX line of FIG. 5.

As described above, the first device 11 is also a surgical treatment instrument which can be used as a handpiece by itself. The grasping portion 22 contains an ultrasound transducer unit 101. The ultrasound transducer unit 101 has a vibration block which is configured into a cylindrical shape so that a plurality of piezoelectric elements 102 each formed into a donut shape are stacked with a plurality of annular electrodes 103 interposed between the adjacent piezoelectric elements. Further, a bolt 104 is inserted through a through-hole in centers of the plurality of piezoelectric elements 102 and the plurality of electrodes 103 which are stacked, and the bolt 104 is screwed into a horn portion 105, whereby the plurality of piezoelectric elements 102 and the plurality of electrodes 103 are firmly brought into close contact with each other to configure the ultrasound transducer unit 101. The ultrasound transducer unit 101 is a unit of a Langevin type bolted ultrasound transducer.

The ultrasound transducer unit 101 is disposed in a cylindrical casing 111. A plurality of signal lines of the plurality of electrodes 103 are connected to some of a plurality of signal lines 2ab in the cable 2a via a connector 112 at a proximal end portion of the casing 111. A distal end side of the horn portion 105 is the probe 21, and a portion 105a from the horn portion 105 to the probe configures an active line of high-frequency output.

As shown in FIG. 5, at a proximal end portion of the horn portion 105, a flange portion 105a is formed. Further, at a predetermined position of an inner periphery of the casing 111, an inward flange portion 111a is formed. A female screw portion 111b is formed on an inner peripheral surface of a distal end portion of the casing 111.

For example, after the signal lines of the plurality of electrodes 103 are connected to the connector 112, the ultrasound transducer unit 101 is inserted from a distal end side of the casing 111. The flange portion 105a of the horn portion 105 abuts on the inward flange portion 111a of the casing 111. With the flange portion 105a and the inward flange portion 111a abutting on each other, the horn portion 105 is fixed to the casing 111 by a cylindrical fixing member 113. More specifically, a male screw portion 113a is formed on an outer peripheral portion of the fixing member 113, and the male screw portion 113a is screwed into the female screw portion 111b of the casing 111, whereby the fixing member 113 presses the horn portion 105 from the distal end side of the casing 111. Thereby, the horn portion 105 is fixed to an inside of the casing 111. A packing 114 made of a rubber material is provided between a proximal end portion of the fixing member 113 and the flange portion 105a. Further, an O-ring 115 is provided at an outer peripheral portion of the fixing member 113. The packing 114 and the O-ring 115 prevent entry of water, blood and the like into the casing 111.

To the distal end side of the casing 111, a cylindrical cap member, that is, a distal end cap 116 is fitted. At an inner peripheral surface of the distal end cap 116, an O-ring 116a is provided to be in close contact with the horn portion 105.

A distal end side of the distal end cap 116 configures the stepped portion 25, and the stepped portion 25 is provided with a plurality of electric armatures 117. Three armatures 117a, 117b and 117c are provided respectively at three stepped portions on an outer peripheral surface of the distal end cap 116, and one armature 117d is provided on an inner peripheral surface. More specifically, on an outer periphery of the stepped portion 25, in sequence from the distal end side of the distal end cap 116, the connection detecting armature 117a to which the signal line for detecting connection of the second device 12 is connected, the active line armature 117b which is connected to the signal line for the active line, and the common armature 117c which is connected to the signal line for the common line of the switch signal are provided. Further, the recovery line armature 117d is provided on the inner peripheral surface of the distal end cap 116. The armature 117d is exposed on a surface of the inner peripheral surface of the distal end cap 116, and is provided on an inner side of the stepped portion 25 so that the conductive member of the second device 12 can be in contact therewith as will be described later.

When the armature 117a is in contact with a corresponding armature of the second device 12 which will be described later, the main body apparatus 3 detects that the second device 12 is fitted to the first device 11. The armature 117a includes two armatures, and when the armature 117a is in contact with an armature 201a at the second device 12 side which will be described later, electrical continuity is formed between the two armatures. The main body apparatus 3 detects the continuity state. More specifically, the armature 117a and the signal line 2ab configure a connection signal output portion or connection signal output means capable of outputting a connection signal DS indicating that the second device 12 is connected to the first device 11. The main body apparatus 3 changes high-frequency output to bipolar output from monopolar output in the case of the high frequency output, and changes ultrasound output to an ultrasound output value at the time of a scissors shape from an ultrasound output value at the time of a spatulate shape in the case of the ultrasound output, based on the connection signal DS.

The three armatures 117a, 117b and 117c are formed in an annular shape along the outer peripheral surface of the stepped portion 25. The armature 117d is provided in an annular shape along the inner peripheral surface of the distal end cap 116.

The armature 117d is in contact with an electric armature (not illustrated) in the second device 12 which will be described later. A tubular member 202 (FIG. 14) made of a conductive material inside the second device 12 is electrically connected to a tubular member made of a conductive material of the insertion portion 2b. Accordingly, the armature 117d is a recovery line armature which is connected to the signal line for the recovery line at the time of high frequency output.

The respective armatures are connected to corresponding wiring of the wiring 2ab in the cable 2a via the conductive members 118 which pass in the distal end cap 116 made of an insulating member and wiring 119 connected to the respective conductive members 118. The conductive member 118 which passes inside the distal end cap 116 is provided inside the distal end cap 116 by insert molding.

An O-ring 120 is provided at the outer peripheral portion of the distal end cap 116. The casing 111 on which the distal end cap 116 is fitted is provided to be inserted through an inside of a second casing 121. The second casing 121 is a cylindrical member the diameter of which becomes smaller toward a proximal end side from a distal end side. The O-ring 120 is in close contact with an inner peripheral surface of the second casing 121, and the first casing 111 and the distal end cap 116 are disposed inside the second casing 121.

Further, on an outer peripheral surface of the distal end side of the second casing 121, a male screw portion 121a is formed. Further, a male screw portion 121b is also formed on an outer peripheral surface of a proximal end side of the second casing 121.

The second casing 121 is further provided inside a third casing 122. The third casing 122 is also a cylindrical member the diameter of which becomes smaller toward a proximal end side from a distal end side. On an outer peripheral surface of the third casing 122, a plurality of projected portions 122a for enhancing the grasping easiness by a surgeon are formed.

A fixing ring 123 and an end cap 124 fix the third casing 122 to hold the third casing 122 therebetween. More specifically, the fixing ring 123 is a cylindrical member made of an insulating member, and has an inward flange portion at a distal end side. A female screw portion 123a is formed on an inner peripheral surface of a proximal end side of the fixing ring 123. The end cap 124 is a cylindrical cap member made of an insulating member, and has a stepped portion on an outer peripheral portion of a distal end side. A female screw portion 124a is formed on an inner peripheral surface at the distal end side of the end cap 124. The male screw portion 121a of the distal end portion of the second casing 121 and the female screw portion 123a of the fixing ring 123 are screwed into each other, and the male screw portion 121b of the proximal end portion of the second casing 121 and the female screw portion 124a of the end cap 124 are screwed into each other, whereby the third casing 122 is fixed to the fixing ring 123 and the end cap 124 to be held therebetween.

As above, the ultrasound transducer unit 101 is disposed in the grasping portion 22.

(Countermeasures Against Heat Generation)

Incidentally, when the first device 11 is in an ultrasound outputting state, the ultrasound transducer unit 101 generates heat. As a result, due to continuous ultrasound output, the heat generated in the ultrasound transducer unit 101 is thermally conducted in the casing of the grasping portion 22, and the temperature of the outer peripheral portion of the grasping portion 22 becomes high. The grasping portion 22 which becomes hot during a surgical operation is likely to cause reduction in operability of the handpiece 2.

Thus, in the first device 11 of the present embodiment, in order to prevent the grasping portion 22 from becoming hot, an air layer is provided between the casings of the grasping portion 22.

As shown in FIG. 8, on an outer peripheral portion of the first casing 111, a plurality of grooves 125 (125a, 125b, 125c) which are extended along an axial direction of the casing 111 are formed. One groove 125a is a groove for positioning with the second casing 121, and a portion which is protruded to an inner peripheral side of the second casing 121 is fitted in the groove 125a, whereby proper positioning of the first casing 111 and the second casing 121 is performed. The four grooves 125b are grooves for passing the conductive members 118 in the distal end cap 116 through. The four grooves 125c are grooves for forming air layers between the first casing 111 and the second casing 121.

As above, the air layers are provided between the first casing 111 and the second casing 121, whereby the heat conduction between the casings is reduced, and a temperature rise in the grasping portion 22 at the time of continuous ultrasound output can be inhibited.

In particular, as shown in FIGS. 4 and 5, the grasping portion 22 of the first device 11 is configured with use of the three casings 111, 121 and 122. The air layers which are positively provided as described above are provided between the first casing 111 and the second casing 121, and therefore, a large heat insulating effect is obtained. Further, an air layer by a clearance is also formed between the second casing 121 and the third casing 122, and therefore, the insulating effect is further increased.

In the present embodiment, the three casings are used, but four or more casings may be used, and the air layers as described above may be positively provided between the adjacent casings.

Further, the air layer is provided between the casings (between the first casing 111 and the second casing 121 in the present embodiment) inside the grasping portion 22, and is covered with the casing at the outermost side (the third casing 122 in the present embodiment), and therefore, when the casing 122 at the outermost side is manufactured by molding, the effect of increasing the degree of freedom of the outer shape of the casing 122 at the outermost side occurs. As a result that the degree of freedom of the outer shape of the casing 122 is increased, the casing can be formed into the shape more excellent in grasping easiness of the grasping portion 22.

Figure 10:
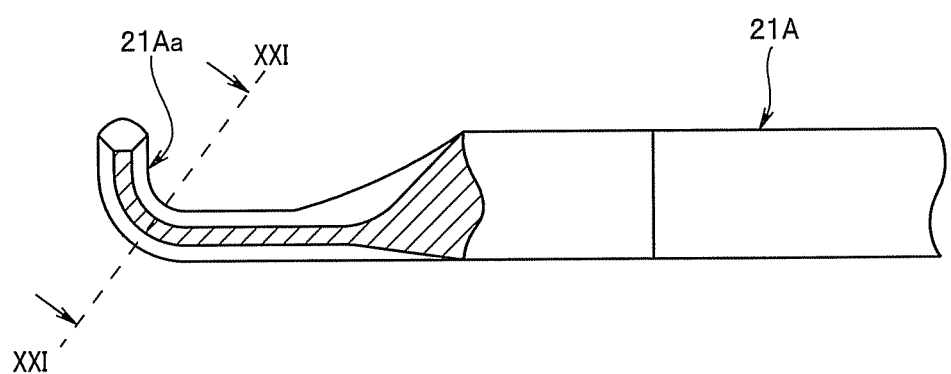
FIG. 10 is a sectional view of a probe 21A with a distal end portion in a hook shape seen from a top surface.

The aforementioned probe 21 is in the spatulate shape as shown in FIG. 4, but may be in a hook shape as shown in FIG. 10. FIG. 10 is a sectional view of a probe 21A with a distal end portion in a hook shape seen from a top surface. A hook portion of the probe 21A is in an S-shape to be capable of inserting the insertion channel 42 of the second device 12 therethrough. An inner side of the hook-shaped portion in the S-shape is a protruding portion with the sectional shape having a predetermined angle, namely, an edge portion.

For each of the components of the first device 11 and the second device 12, a material adaptable to high-temperature and high-pressure steam sterilization, that is, autoclaving, for example, super engineering plastics or the like is used. However, if the first device 11 and the second device 12 are of a disposal type, each component may be a component of an ordinary resin material.

(Connection Structure of the Connector Portion 23 and the Connector Portion 3a)

Next, a connection structure of the connector portion 23 of the first device 11 and the connector portion 3a of the main body apparatus 3 will be described.

Figure 11:
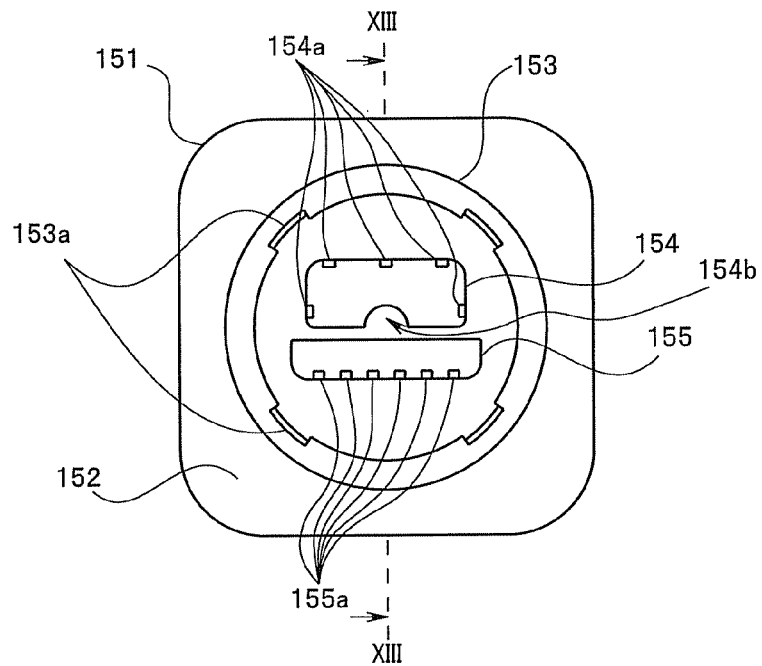
FIG. 11 is a front view of a plug 151 in a connector portion 23.
Figure 12:
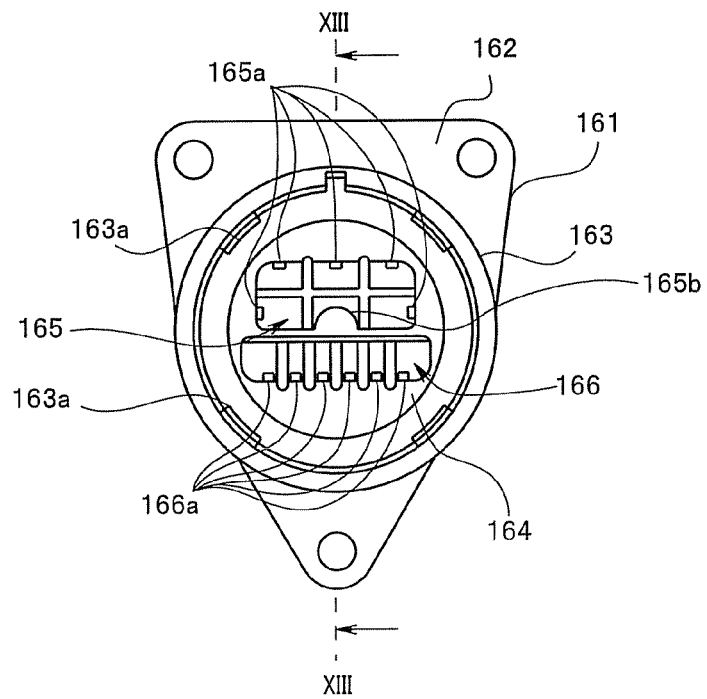
Figure 13:
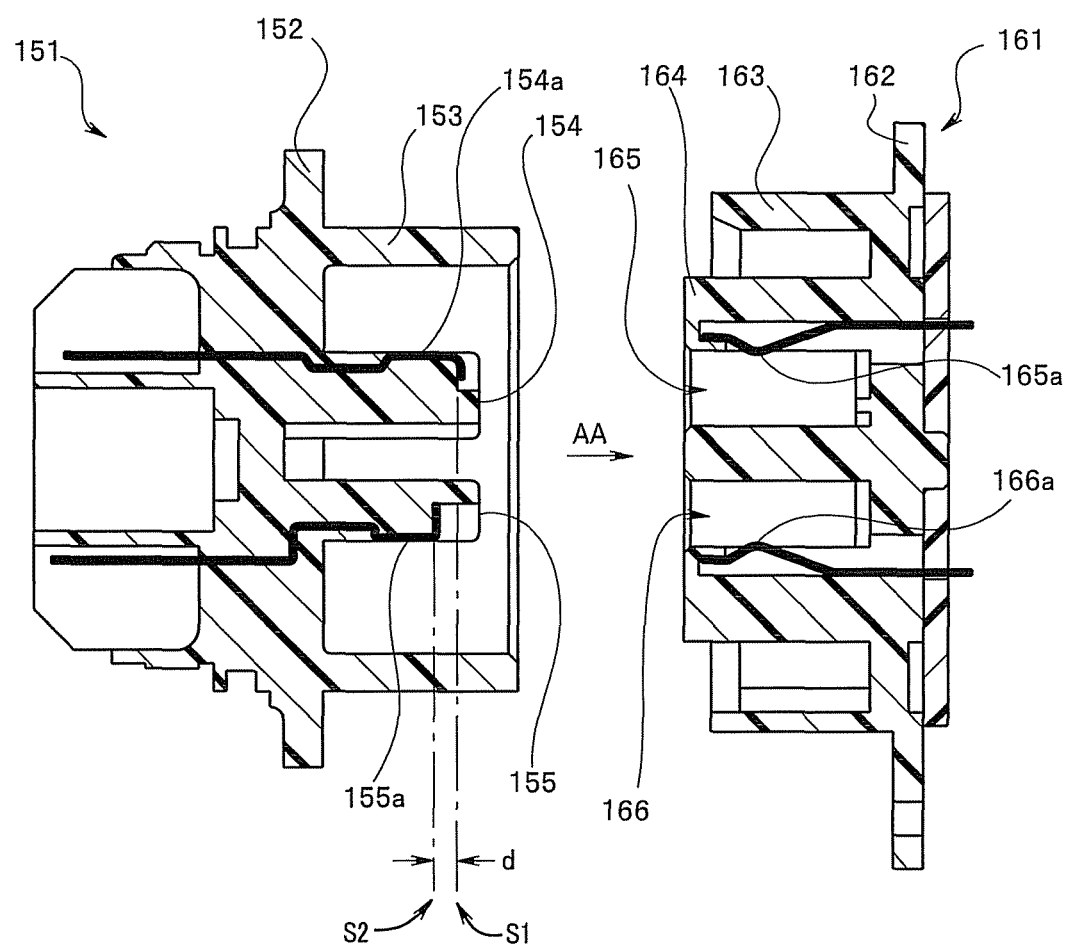
FIG. 13 is a sectional view taken along lines XIII-XIII of FIGS. 11 and 12 for explaining connection of the plug 151 and the receptacle 161.

FIG. 11 is a front view of a plug 151 in the connector portion 23. FIG. 12 is a front view of a receptacle 161 in the connector portion 3a. FIG. 13 is a sectional view taken along XIII-XIII lines of FIGS. 11 and 12 for explaining connection of the plug 151 and the receptacle 161.

The connector portion 23 of the first device 11 has the plug 151. As shown in FIGS. 11 and 13, the plug 151 has a cylindrical portion 153 with a center axis provided in a direction orthogonal to a plane of a base portion 152. Further, the plug 151 has two protruding portions 154 and 155 which are protruded from the base portion 152. The first protruding portion 154 has a plurality of output terminals 154a for drive signals, and the second protruding portion 155 has a plurality of terminals 155a for switch signals and connection detecting signals. Each of a plurality of terminals 154a and 155a is connected to the corresponding signal line of the signal lines 2ab in the cable 2a. The first protruding portion 154 and the second protruding portion 155 are formed inside the cylindrical portion 153. Further, a plurality of claw portions 153a which are engaged with engaging portions 163a (FIG. 12) which are provided at predetermined portions of the connector 3a are formed at a periphery of the cylindrical portion 153.

The connector 3a has the receptacle 161. As shown in FIGS. 12 and 13, the receptacle 161 has a cylindrical portion 163 with a center axis provided in the direction orthogonal to a plane of a base portion 162. Further, the receptacle 161 has a protruding portion 164 which is protruded from the base portion 162. The protruding portion 164 has two recessed portions 165 and 166. The two recessed portions 165 and 166 are formed toward the base portion 162 from a distal end side of the protruding portion 164. The protruding portion 164 is formed inside the cylindrical portion 163. A plurality of engaging portions 163a which are engaged with the plurality of claw portion 153a are provided at an inner peripheral portion of the cylindrical portion 163.

The recessed portion 165 has a plurality of output terminals 165a for drive signals on an inner peripheral surface thereof, and the recessed portion 166 has a plurality of terminals 166a for switch signals and connection detection signals on an inner peripheral surface thereof. The respective terminals 165a and 166a are connected to corresponding circuits of the main body apparatus 3 by corresponding signal lines.

Further, a groove portion 154b with a semi-circular section is formed at the protruding portions 154 of the plug 151 so that the plug 151 is inserted into the receptacle 161 in a correct orientation. The groove portion 154b is formed parallel with the direction orthogonal to the plane of the base portion 152.

Meanwhile, at an inner peripheral portion of the recessed portion 165 of the receptacle 161, a projected portion 165b in a semi-columnar shape which is engaged with the groove portion 154b is formed. Accordingly, only when the projected portion 165b in a semi-columnar shape is in the position where the projected portion 165b is fitted in the groove portion 154b of the plug 151, the plug 151 is inserted into the receptacle 161 in a correct orientation, and the connector portion 23 can be fitted in the connector portion 3a.

An identifying element for identifying the kind of the first device 11, for example, a resistor is provided in the first device 11, for example, in the plug 151, though not illustrated. The resistor not illustrated is connected to the two terminals 155a for detecting connection. When the plug 151 is fitted in the receptacle 161, the two terminals 155a and the two corresponding terminals 166a at the receptacle 161 side are electrically connected, and connection of the first device 11 and the kind of the connected first device 11 can be detected in the main body apparatus 3. Furthermore, instead of the resistor, only the wiring which connects the two terminals 155a for detecting connection may be used. In that case, the main body apparatus 3 can detect connection or non-connection of the device.

Incidentally, when the first device 11 is connected to the apparatus main body 3, the plug 151 is not sometimes suitably engaged with the receptacle 161. For example, when the plug 151 is in a state in which the plug 151 is almost disengaged from the receptacle 161, there can be a state in which a clearance is formed between the output terminals of the drive signal.

In such a state, for example, when a surgeon turns on the switch of high-frequency output, there is the fear of occurrence of an electrical spark in the clearance between the terminals for a high-frequency current in the plug 151 and the receptacle 161. Occurrence of such a spark leads to breakage or a failure of the plug 151 and the receptacle 161.

Thus, in the present embodiment, disposition of the terminals in the plug 151 and the terminals in the receptacle 161 is devised.

As shown in FIG. 13, when the connector portion 23 is fitted in the connector portion 3a, the plug 151 moves to the receptacle 161 in a fitting direction shown by the arrow AA. The plurality of output terminals 154a for drive signals and the plurality of terminals 165a for switch signals and connection detection signals are disposed at the outer peripheral portions of the protruding portions 154 and 155 so that a position S1 where the plurality of output terminals 154a for drive signals in the plug 151 are first brought into contact with the plurality of output terminals 165a for drive signals of the receptacle 161, and a position S2 where the plurality of terminals 155a for switch signals and connection detection signals in the plug 151 are first brought into contact with the plurality of terminals 166a for switch signals and connection detection signals in the receptacle 161 are displaced in the fitting direction AA, namely, have an offset.

In FIG. 13, the position S1 where the plurality of output terminals 154a are first brought into contact with the plurality of output terminals 165a is separated by a distance d from the base portion 152 more than the position S2 where the plurality of terminals 155a are first brought into contact with the plurality of terminals 166a. The distance d is, for example, 0.8 mm.

Thereby, when the connector portion 23 is fitted in the connector portion 3a, the plurality of terminals 155a for switch signals and connection detection signals are brought into contact with the plurality of terminals 166a after the plurality of output terminals 154a for drive signals are brought into contact with the plurality of output terminals 165a.

As above, the first device 11 has the plug 151 as the connector portion for being connected to the main body apparatus 3, and the main body apparatus 3 has the receptacle 161 as the connector to which the plug 151 is connected. The armature which supplies a drive signal is disposed at a position which is displaced along the connection direction with respect to the armature which transmits an instruction signal so that the armatures which transmit instruction signals for instruction of output of drive signals are brought into contact with each other after the armatures which supply drive signals to the plug 151 are brought into contact with each other when the plug 151 and the receptacle 161 are connected along a predetermined connecting direction.

Accordingly, for example, even when the plug 151 is in a state in which the plug 151 is almost disengaged from the receptacle 161, the output terminals of a high-frequency current are connected to each other without fail when a switch signal is detected in the apparatus main body 3. As a result, occurrence of an electrical spark can be prevented in the clearance between the output terminals for drive signals in the plug 151 and the receptacle 161 when a surgeon turns on the switch of high-frequency output.

(Second Device)

A configuration of the second device 12 will be described in detail.

Figure 14:
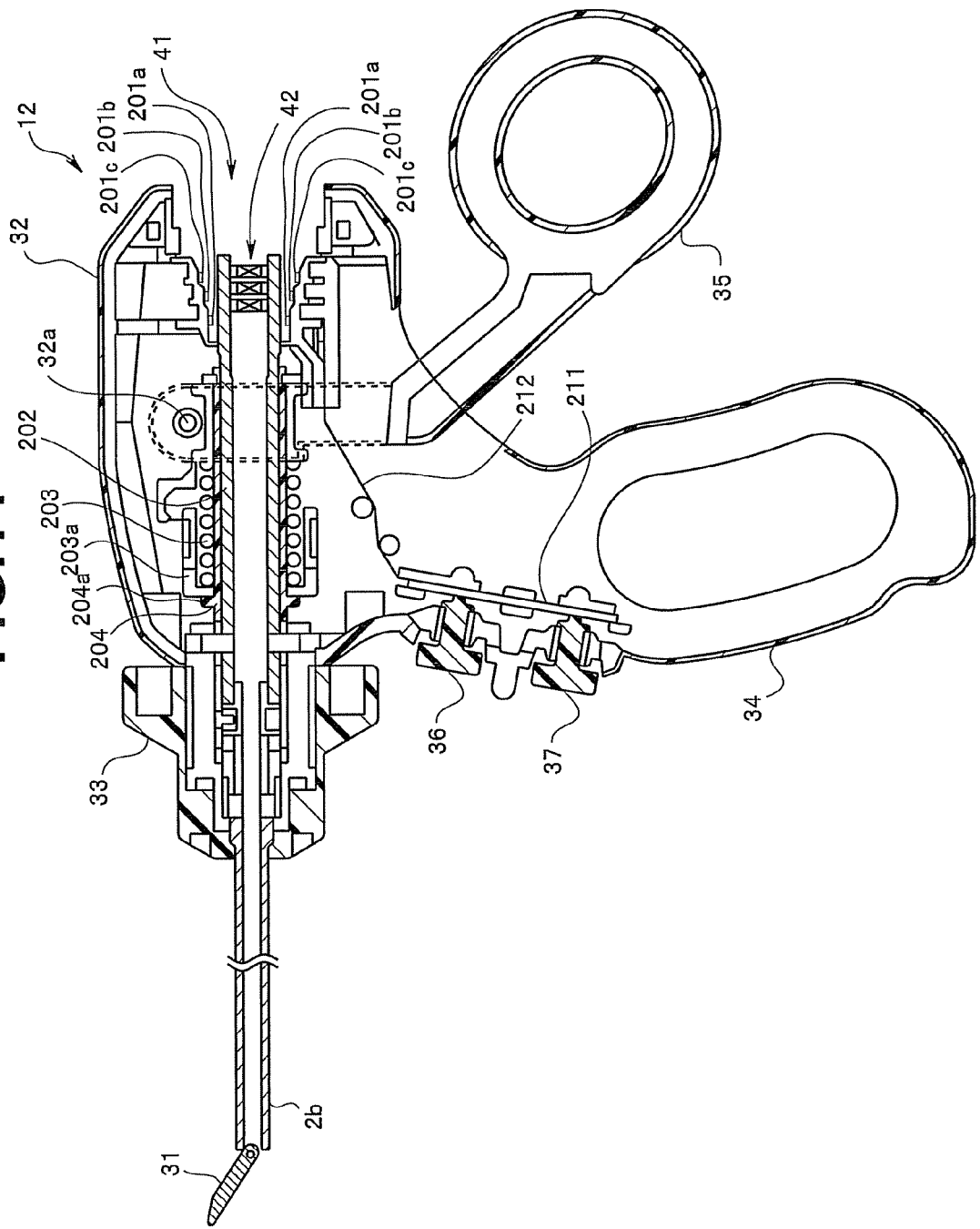
FIG. 14 is a sectional view of a second device 12.

FIG. 14 is a sectional view of the second device 12. Three electric armatures 201a, 201b and 201c are provided on an inner peripheral surface of the recessed portion 41 of the operation portion main body 32. The three armatures 201a, 201b and 201c are respectively armatures corresponding to the three armatures 117a, 117b and 117c of the first device 11. The three armatures 201a, 201b and 201c are provided on the inner peripheral surface of the recessed portion 41 so as to be in contact with the three armatures 117a, 117b and 117c of the first device 11 respectively when the first device 11 is fitted in the second device 12.

The tubular member 202 with a center axis coaxial with the axis of the insertion portion 2b is provided in the operation portion main body 23. The tubular member 202 is formed from a conductive material. A cutout portion not illustrated is formed at a proximal end side of the tubular member 202, and the second device 12 is configured so that the stepped portion 25 is engaged with the recessed portion 41 when the first device 11 is inserted from the proximal end side of the tubular member 202. An inner side of the tubular member 202 and an inner side of the insertion portion 2b form an insertion channel 42.

A spring member 203 is provided on an outer peripheral portion of the tubular member 202 via a tubular member 204. More specifically, the tubular member 202 is inserted through the tubular member 204 made of an insulating material, and the tubular member 204 is inserted through an inner side of the spring member 203. A flange portion 204a is formed at an outer peripheral portion of the tubular member 204. A distal end side of the spring member 203 abuts on the flange portion 204a via a spring bearing member 203a. A proximal end side of the spring member 203 abuts on a portion in the vicinity of the pin 32a of the movable handle 35, and the spring member 203 is provided in the operation portion main body 32 to press the movable handle 35. As a result, the spring member 203 is a constant-force spring which urges the handle 35 with a constant force in the direction to separate the movable handle 35 from the fixed handle 34, in other words, in a counterclockwise direction around the pin 32a in FIG. 14. More specifically, the spring member 203 configures urging means which urges the movable handle 35 to rotate in the direction in which the handle portion 2c opens with the pin 32a as a center of rotation.

Further, a distal end portion of the tubular member 202 is electrically connected to the insertion portion 2b. The tubular member 202 is formed to be electrically connected to the armature 117d which is exposed on the surface of the stepped portion 25 of the first device 11 when the first device 11 and the second device 12 are coupled with each other. Accordingly, at the time of bipolar output of high-frequency output, the movable jaw 31, the insertion portion 2b and the tubular member 202, the armature 117d, and the conductive member 118 and the cable 2a configure a recovery line.

The switches 36 and 37 are connected to the active line armature 201b and the common line armature 201c through a circuit substrate 211 of the operation portion main body 32 and a signal line 212. Accordingly, if a surgeon presses the switch 36 with a thumb at the time of high-frequency output, for example, a switch signal for outputting high-frequency output from the probe 21 is transmitted to the main body apparatus 3 through the armatures 201b and 117b, the conductive member 118 and the cable 2a. Accordingly, when the switch 36 is pressed, the probe 21 outputs high-frequency output. Further, when the switch 37 is pressed, the output value of high-frequency output of the probe 21 is changed.

(Modified Example of the Second Device)

Figure 15:
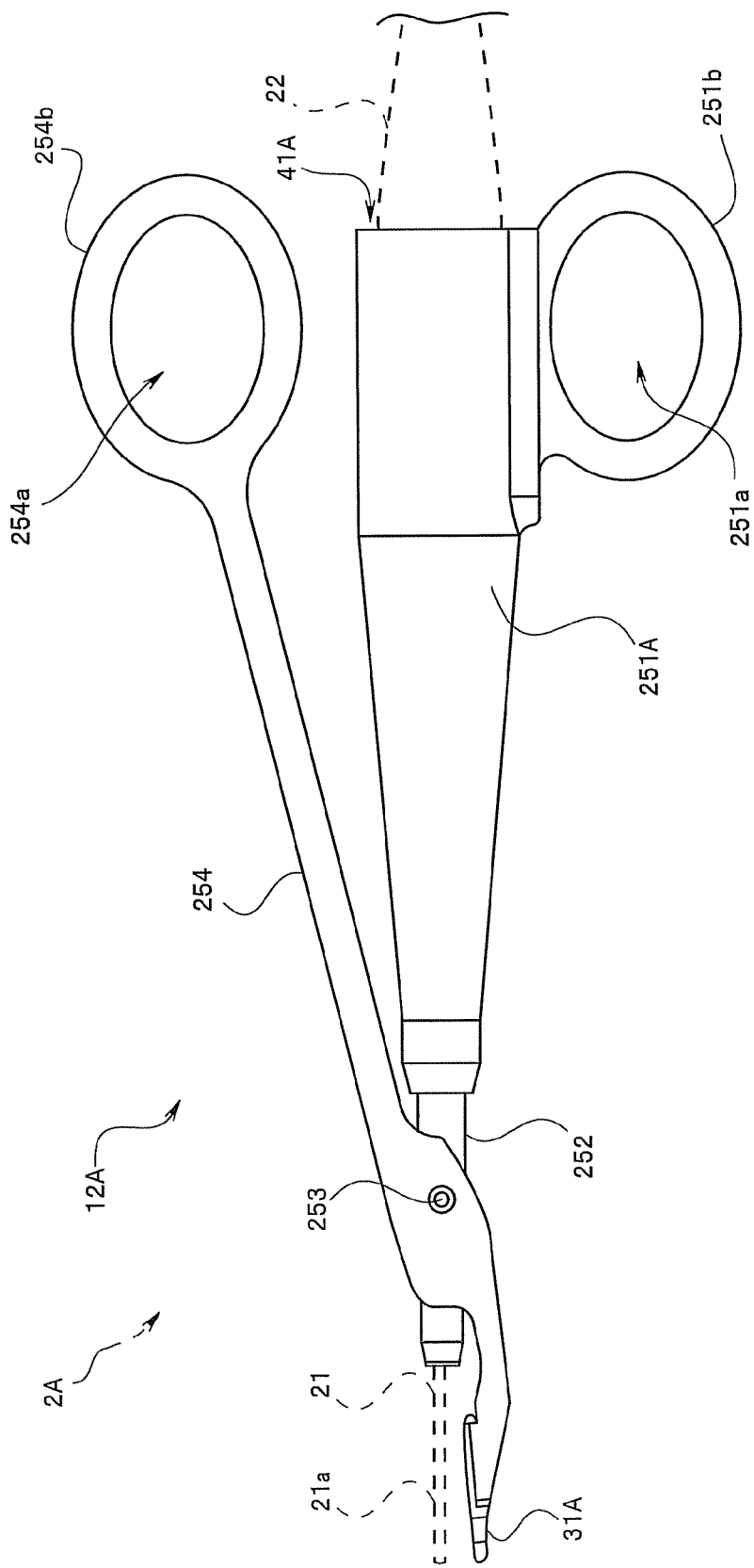
FIG. 15 is a front view according to a modified example of the second device of the present embodiment.

FIG. 15 is a front view according to a modified example of the second device of the present embodiment. The aforementioned handpiece 2 is for use under observation of so-called laparoscope, and a second device 12A shown in FIG. 15 is a device for configuring a handpiece for celiotomy. The second device 12A according to the modified example is configured by having a cylindrical portion 251A having a taper portion at a distal end side, a tubular portion 252 provided at a distal end portion of the cylindrical portion 251A, and a movable member 254 pivotally supported by a pin 253 provided at an outer peripheral portion of the tubular portion 252.

A fixed handle 251b having a finger rest hole 251a at which the finger of a surgeon is rested is provided at an outer peripheral portion of the cylindrical portion 251. An opening portion 41A of a proximal end portion of the cylindrical portion 251 is an opening for inserting the first device 11 from the probe 21. As shown by a dotted line in FIG. 15, the treatment portion 21a of the probe 21 of the first device 11 which is inserted from the cylindrical portion 251 is protruded from a distal end portion of the cylindrical portion 251.

A movable handle 254b having a finder rest hole 254a at which the thumb of a surgeon is rested is provided at a proximal end side of the movable member 254. A movable jaw 31A is provided at a distal end side of the movable member 254.

An inner peripheral surface of the opening portion 41A of the cylindrical portion 251 of the second device 12A has a shape corresponding to the stepped portion 25 and a plurality of electric armatures similarly to those of the aforementioned second device 12. The probe 21 of the first device 11 is inserted from the opening portion 41A, whereby the first device 11 can be fitted in the second device 12A. The first device 11 is fitted in the second device 12A, whereby a scissors-shaped handpiece 2A for use at the time of celiotomy is configured.

With the first device 11 fitted in the second device 12A, a surgeon can open and close a treatment portion configured by the movable jaw 31A and the treatment portion 21a of the distal end portion of the probe 21 by operating the movable handle 254b.

In the second device 12 shown in FIGS. 2 and 14, the switches 36 and 37 are provided at the operation portion main body 32. In the case of the second device 12A of FIG. 15, two switches (not illustrated) corresponding to the switches 36 and 37 may be provided at the outer peripheral portion of the grasping portion 22 of the first device 11.

Figure 16:
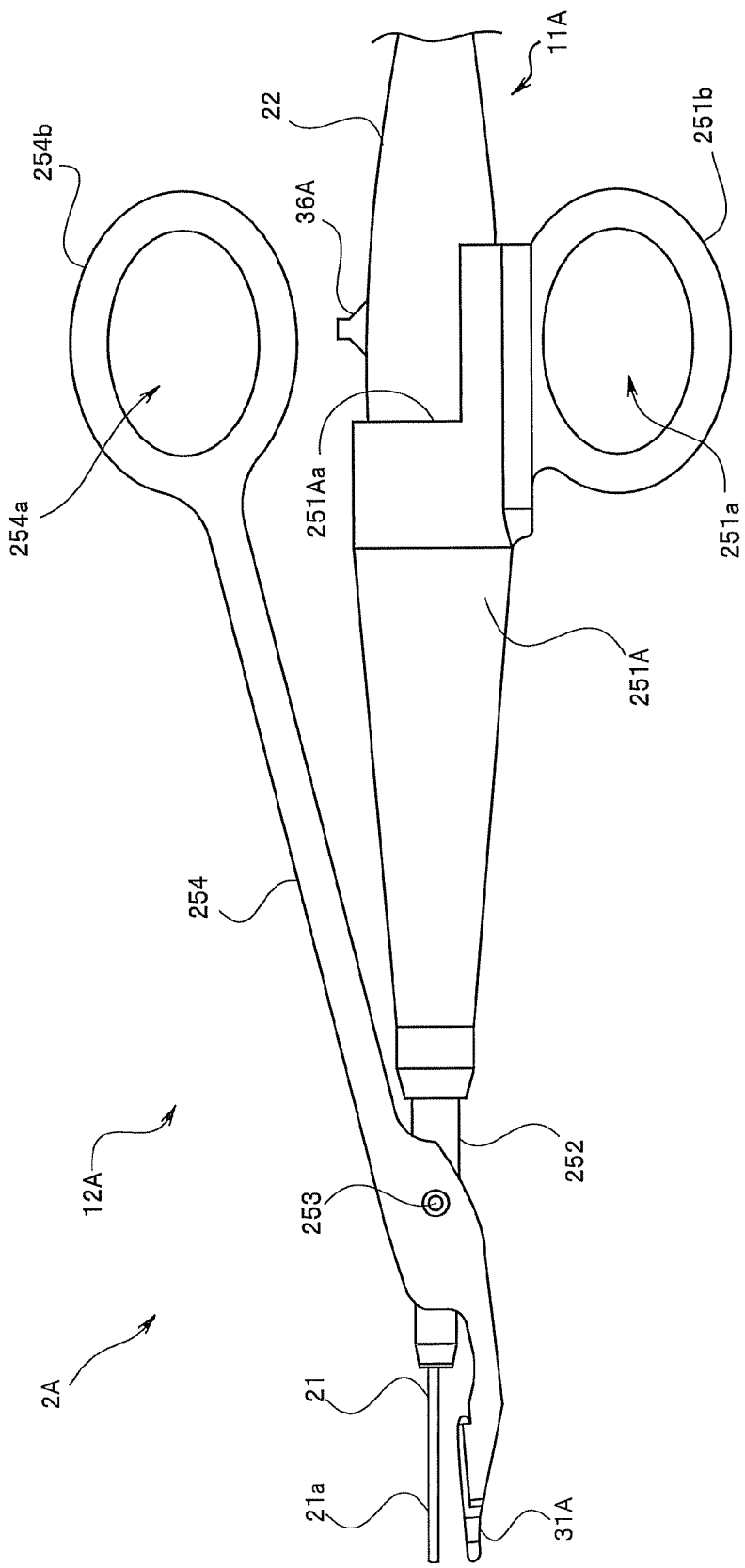
FIG. 16 is a view for explaining a modified example in the case in which a switch is provided at a position where a movable handle of the first device abuts.

Further, in consideration of operability, the switch corresponding to the switch 36 for high-frequency output may be provided at a position where the movable handle 254b abuts in the operation portion of the first device 11 in the state in which the first device is fitted in the second device as shown in FIG. 16. More specifically, the grasping portion 22 is provided with a switch for giving an instruction to output at least one of an ultrasound vibration and a high-frequency current, and the switch may be disposed at the position where the switch can be pressed by the movable handle configuring the handle portion of the second device 12B in the operation portion main body which is the grasping portion when a second device 12B is fitted.

FIG. 16 is a view for explaining a modified example when the switch is provided at a position on which the movable handle of the first device abuts. A first device 11A is provided with a switch 36A at a position which is on a side surface of the grasping portion 22, and which the movable handle 254b abuts on when the movable handle 254b is closed in the state in which the first device 11A is fitted in the second device 12B. Accordingly, as shown in FIG. 16, a cutout portion 251Aa is formed at a part of a proximal end portion of a cylindrical portion 251A so that the switch 36A is exposed.

Accordingly, a surgeon can give an instruction to output high-frequency output by only performing a closing operation of the movable handle 254b in the handpiece for use at the time of celiotomy, and therefore, favorable operability is provided. In particular, only an operation of closing the movable handle 254b can be performed with one hand, and therefore, the operation of turning on the switch for high-frequency output with a free finger is not required, and therefore, the treatment portion at the distal end of the handpiece does not become shaky.

Figure 17:
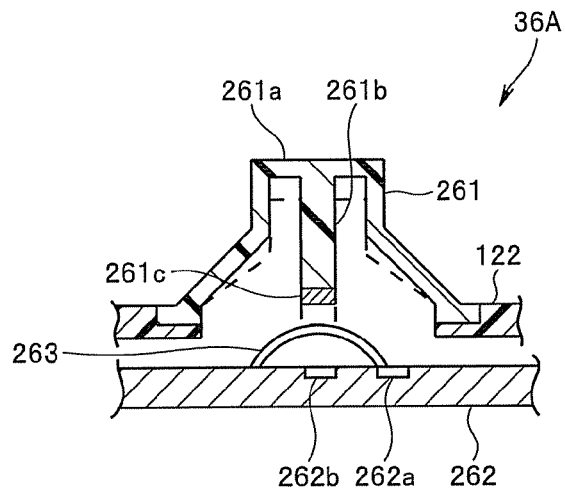
FIG. 17 is a sectional view for explaining a configuration of a switch 36A.
Figure 18:
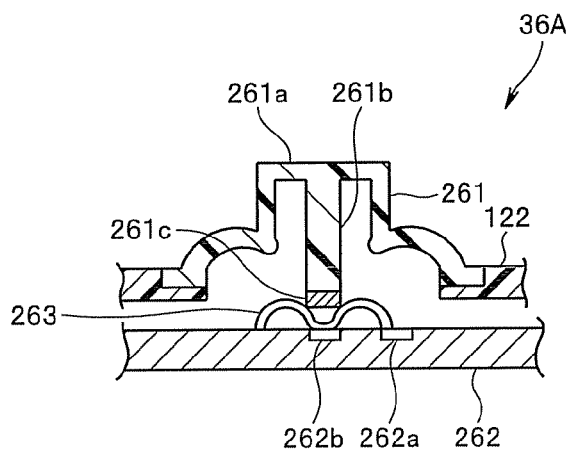
FIG. 18 is a sectional view for explaining the configuration of the switch 36A.
Figure 19:
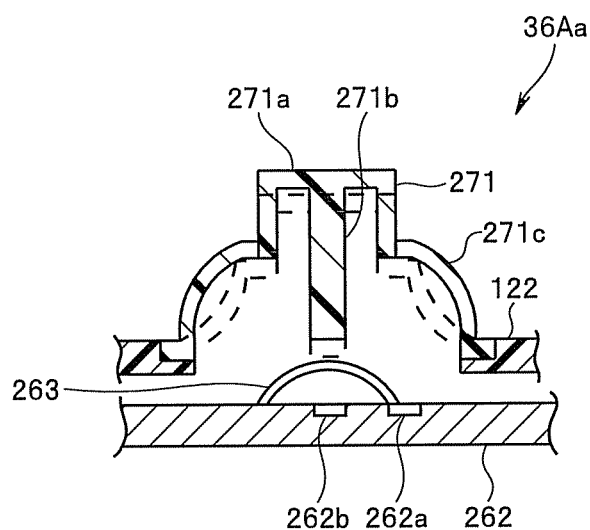
FIG. 19 is a sectional view showing a modified example of the switch 36A.

In this case, the switch 36A is preferably a two-stage switch. FIGS. 17 to 19 are views for explaining the configuration of the switch 36A that is a two-stage switch provided at the first device.

FIGS. 17 and 18 are sectional views for explaining the configuration of the switch 36A. As the switch 36A, a substantially conical pressing member 261 which is made of a rubber member or the like and has a flat portion 261a which is flat at a distal end is provided to protrude on a surface of a casing 122 of the grasping portion 22. A protruding portion 261b is formed on an inner side of the pressing member 261, that is, on a back side of the flat portion 261a. A conductive metal member 261c is provided at a distal end portion of the protruding portion 261b. The metal member 261c is connected to wiring not illustrated.

A substrate 262 is placed inside the casing 122. A disk member 263 made of a conductive metal material is provided at a position opposed to a protruding portion 261b on the substrate 262. The disk member 263 is not a flat member, but has a shape curved to be along a surface of a sphere with a central portion protruded in a direction of the protruding portion 261b. The disk member 263 is connected to wiring 262a on the substrate 262, and a contact point 262b which is connected to wiring not illustrated is provided on the substrate 263 under the disk member 263.

Since the pressing member 261 is made of a rubber member or the like, the pressing member 261 is deformed when pressed from above. As shown by the dotted line of FIG. 17, when the pressing member 261 is deformed, the metal member 261c at the distal end of the protruding portion 261b is brought into contact with the disk member 263. By the contact, the wiring connected to the metal member 261c and the wiring 262a of the disk member 263 are electrically continued, and therefore, the main body apparatus 3 can detect the continuity. When the main body apparatus 3 detects the contact of the metal member 261a and the disk member 263, the main body apparatus 3 outputs a sound for informing the surgeon of the contact (hereinafter, called a first sound) by the sound through a speaker.

When the pressing member 261 is further pressed, the protruding portion 261b further presses the disk member 263, and the disk member 263 is deformed. As shown in FIG. 18, the disk member 263 is deformed, and the central portion of the disk member 263 is brought into contact with the contact point 262b on the substrate. Since the contact point 262b is connected to the wiring not illustrated, the wiring connected to the contact point 262b and the wiring 262a of the disk member 263 are electrically continued by the contact. Accordingly, the main body apparatus 3 detects the continuity, and outputs a sound for informing a surgeon of the contact by a second sound different from the first sound through the speaker, and starts output of a high-frequency current. The second sound is outputted while the central portion of the disk member 263 is in contact with the contact point 262b on the substrate.

When the pressing member 261 is not pressed, the pressing member 261 which is an elastic member returns to the original shape as shown by the solid line of FIG. 17, and the disk member 263 also returns to the original shape as shown by the solid line of FIG. 17. As above, the switch 36A is a two-stage switch which outputs electrical switch signals at the first stage and the second stage.

As above, the two-stage switch is used as the switch 36A, the surgeon can recognize that the surgeon grasps the handle portion to close the handle portion by the first sound, and further can recognize that high-frequency output is started by the second sound. In other words, since the main body apparatus 3 makes the surgeon recognize that the surgeon grasps the handle portion by informing the surgeon of it by the first sound, and allows high-frequency output to be performed thereafter, the surgeon can reliably perform an operation of high-frequency output.

FIG. 19 is a sectional view showing a modified example of the switch 36A. The switch shown in FIG. 19 is also a two-stage switch, and is a switch which generates a mechanical sound at the first stage. The same components as those in FIGS. 17 and 18 are assigned with the same reference numerals and characters, and description thereof will be omitted. As shown in FIG. 19, as a switch 36Aa, a substantially conical pressing member 271 which is made of a thin metal or the like and has a flat portion 271a which is flat at a distal end is provided to protrude on the surface of the casing 122 of the grasping portion 22. A protruding portion 271b is formed on an inner side the pressing member 271, that is, on a back side of the flat portion 271a. A side surface portion 271c of the pressing member 271 is in a shape slightly swelled outside as shown by the solid line of FIG. 19 when the pressing member 271 is not pressed.

However, the side surface portion 271c has the shape which is deformed to be recessed inside suddenly at a certain point of time as shown by the dotted line in FIG. 19 as the pressing member 271 is gradually pressed from above and the stress of deformation is exerted thereon. At the time of instantaneous deformation of the side surface portion 271c, a mechanical sound is generated.

When the pressing member 271 is further pressed, the protruding portion 271b presses the disk member 263, the disk member 263 is deformed, the disk member 263 is deformed as shown by the dotted line in FIG. 19, and the central portion of the disk member 263 is brought into contact with the contact point 262b on the substrate. By the contact, the wiring connected to the contact point 262b and the wiring 262a of the disk member 263 are electrically continued, and the main body apparatus 3 detects the continuity. The main body apparatus 3 outputs a sound for informing the surgeon of the contact through the speaker, and starts output of a high-frequency current. The sound is outputted while the central portion of the disk member 263 is in contact with the contact point 262b on the substrate.

When the pressing member 261 is not pressed, the pressing member 271 which is an elastic member returns to the original shape as shown by the solid line of FIG. 19, and the disk member 263 also returns to the original shape. As above, the switch 36Aa is a two-stage switch which generates a mechanical sound at the first stage, and outputs an electrical switch signal at the second stage.

As above, by using the two-stage switch as described above, the surgeon can reliably perform an operation of high-frequency output.

(Treatment Portion)

Next, a configuration of the treatment portion will be described.

The handpiece 2 according to the present embodiment is capable of simultaneously outputting ultrasound output and high-frequency output. The treatment portion 21a of the spatulate probe 21 is used in some cases for ultrasound output, in some cases for high-frequency output, and in some cases for simultaneous output of ultrasound and high frequency. Further, the probe 21 has the case of configuring the scissors-shaped treatment portion in corporation with the movable jaw 31. In this case, the movable jaw 31 and the treatment portion 21a of the probe 21 are used in some cases for ultrasound output, in some cases for high-frequency output and in some cases for simultaneous output of ultrasound and high frequency. Accordingly, the treatment portion 21a and the jaw member 31 have suitable shapes corresponding to such use states.

Figure 20:
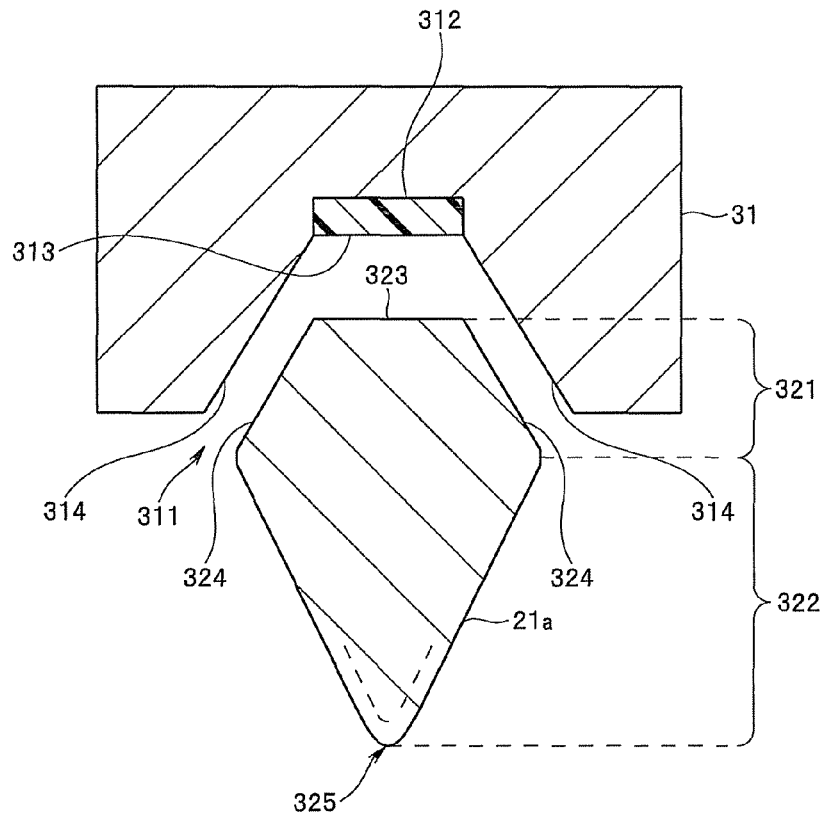
FIG. 20 is a sectional view of a treatment portion 21a and a jaw member 31 taken along a XX-XX line of FIG. 2.

FIG. 20 is a sectional view of the treatment portion 21a and the jaw member 31 taken along a XX-XX line of FIG. 2. The jaw member 31 has a groove 311 in which part of the insertion probe 21 is engaged, along an axial direction. The groove 311 has a wide channel shape with a wide opening in a section orthogonal to an axis of the jaw member 31. The jaw member 31 is made of a conductive material, and an insulating member 312 is provided in a range where the treatment portion 21a is in contact along the axial direction on a bottom surface portion 313 of the channel shape.

The treatment portion 21a has a rhombic shape partially cut out in the section orthogonal to the axial direction. The sectional shape of the treatment portion 21a is a shape which is cut out in the direction orthogonal to a longer diagonal line of the rhombic shape as shown in FIG. 20. The treatment portion 21a with part of the rhombic shape cut out in the sectional shape has a trapezoidal portion 321 which is engaged in the groove 311 of the jaw member 31. A portion in which part of the rhombic shape is not cut out in the sectional shape is an isosceles triangle portion 322 in the shape of a substantially isosceles triangle of the treatment portion 21a.

When the handle portion 2c is closed, the treatment portion 21a and the jaw member 31 are fitted to each other. When they are fitted, the bottom surface portion 313 of the channel-shaped groove 311 abuts on a top surface portion 323 of the trapezoidal portion 321 of the treatment portion 21a, and two inner wall portions 314 of the channel-shaped groove 311 abut on inclined surface portions 324 of the trapezoidal portion 321.

Further, an apex portion 325 of the isosceles triangle portion 322 of the treatment portion 21a is formed to be rounded, but the apex portion 325 has a slightly sharp angle.

When the first device 11 is used as a spatulate ultrasound treatment instrument, the entire treatment portion 21a acts as an ultrasound vibration treatment portion, and the apex portion 325 and its peripheral portion (shown by the dotted line) particularly act as a scalpel knife to the tissue of the treatment object.

Further, when the first device 11 is used as a spatulate high-frequency treatment instrument, the apex portion 325 and its peripheral portion (shown by the dotted line) act as an electric scalpel knife to the tissue of the treatment object.

When the handpiece 2 is used as a scissors-shaped ultrasound treatment instrument, the bottom surface portion 313 and the inner wall portions 314, and the top surface portion 323 and the inclined surface portions 324 act as the working surfaces of an ultrasound vibration.

Further, when the handpiece 2 is used as the scissors-shaped high-frequency treatment instrument, the inner wall portions 314 and the inclined surface portions 324 act as the working surfaces of a bipolar high-frequency current.

When the first device 11 is used as the spatulate treatment instrument of simultaneous output of ultrasound and high frequency, the entire treatment portion 21a acts as the ultrasound vibration treatment portion, and the apex portion 325 and its peripheral portion (shown by the dotted line) particularly act as an electrical scalpel knife to the tissue of the treatment object.

Further, when the handpiece 2 is used as the scissors-shaped treatment instrument of simultaneous output of ultrasound and high frequency, the bottom surface portion 313 and the top surface portion 323 act as the working surfaces of an ultrasound vibration, and the inner wall portions 314 and the inclined surface portions 324 act as the working surfaces of a bipolar high-frequency current.

Consequently, according to the configuration of the treatment portion shown in FIG. 20, excellent operability is provided not only in the case of use of the first device 11 as an ultrasound treatment instrument or a high-frequency treatment instrument, but also in the case of use of the first device and the second device 12 by being connected as a scissors-shaped ultrasound treatment instrument or high-frequency treatment instrument, and further in the case of use of the first device 11 and the second device 12 by being connected as a scissors-shaped treatment instrument for the time of simultaneous output of ultrasound and high frequency.

When the scissors-shaped surgical treatment instrument made by the first device and the second device being coupled to each other performs high-frequency output or simultaneous output of high frequency and ultrasound, monopolar output may be enabled instead of bipolar output as the high-frequency output.

Figure 21:
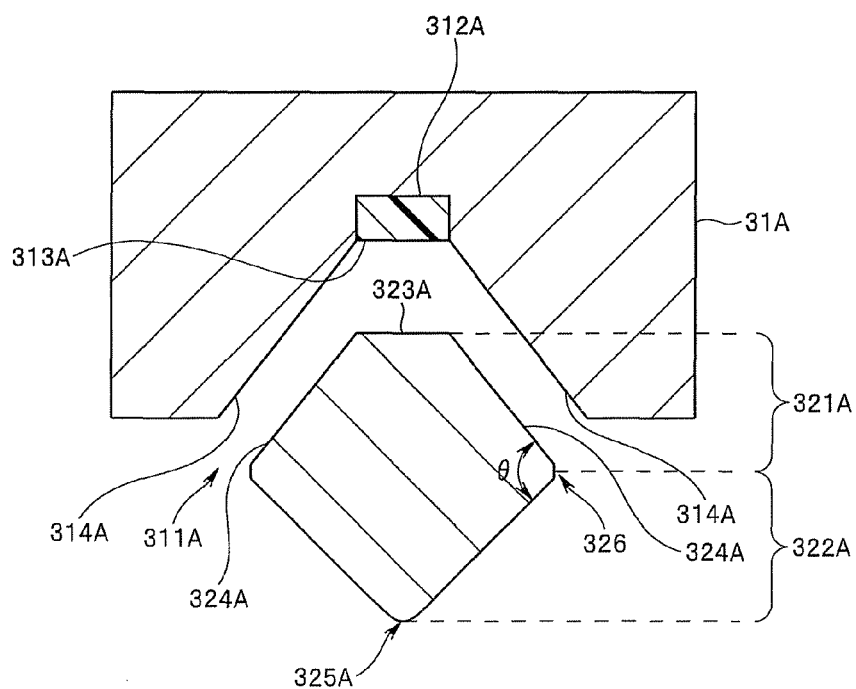
FIG. 21 is a view for explaining a configuration of the treatment portion in the case of a hook-shaped probe 21A.

FIG. 21 is a view for explaining a configuration of the treatment portion in the case of a hook-shaped probe 21A. More specifically, FIG. 21 is a sectional view of a treatment portion 21Aa and a jaw member 31A taken along a line XXI-XXI in FIG. 10. FIG. 10 shows only the treatment portion 21Aa, but FIG. 21 shows a section of the treatment portion 21Aa and the jaw member 31A in the case of the scissors-shaped treatment instrument. The jaw member 31A has a groove 311A in which part of the treatment portion 21Aa is engaged, along an axial direction. The groove 311A has a channel shape with a wide opening in a section orthogonal to an axis of the jaw member 31A. The jaw member 31A is made of a conductive material, and an insulating member 312A is provided along the axial direction on a bottom surface portion 313A of the channel shape.

The treatment portion 21Aa has a rhombic shape partially cut out in the section orthogonal to the axial direction. The sectional shape of the treatment portion 21Aa is a shape in which part of the rhombic shape is cut out in the direction orthogonal to one diagonal line as shown in FIG. 21. The treatment portion 21Aa with part of the rhombic shape cut out in the sectional shape has a trapezoidal portion 321A which is engaged in the groove 311A of the jaw member 31A. A portion in which part of the rhombic shape is not cut out in the sectional shape is an isosceles triangle portion 322A of the probe 21A.

When the handle portion 2c is closed, the treatment portion 21Aa and the jaw member 31A are fitted to each other. When they are fitted, the bottom surface portion 313A of the channel-shaped groove 311A abuts on a top surface portion 323A of the trapezoidal portion 321A of the treatment portion 21Aa, and two inner wall portions 314A of the channel-shaped groove 311A abut on inclined surface portions 324A of the trapezoidal portion 321A.

Further, an apex portion 325A of the isosceles triangle portion 322A of the treatment portion 21Aa is formed to be rounded, but an apex portion 326 of the inner side of the hook shape has a slightly sharp angle. An angle $\theta$ of the apex portion 326 is preferably 45 degrees to 100 degrees. 45 degrees is a strength limit of the probe 21A. As above, the apex portion 326 of the treatment portion 21Aa configures a protruding portion having a predetermined angle at the inner side of the hook-shaped portion, that is, an edge portion.

The treatment portion in the hook shape is often used for dissection. The apex portion 326 of the probe 21A becomes a working portion at the time of dissection. Since the apex portion 326 has the slightly sharp angle $\theta$, the apex portion 326 is effective for dissection treatment.

The treatment portion 21Aa and the jaw member 31A shown in FIG. 21 perform the same operation as the treatment portion 21a and the jaw member 31 shown in FIG. 20 at the time of ultrasound output, at the time of high-frequency output, and at the time of simultaneous output of ultrasound and high frequency respectively, except for the aforementioned operation at the time of dissection.

(Configuration of Apparatus Main Body)

Figure 22:
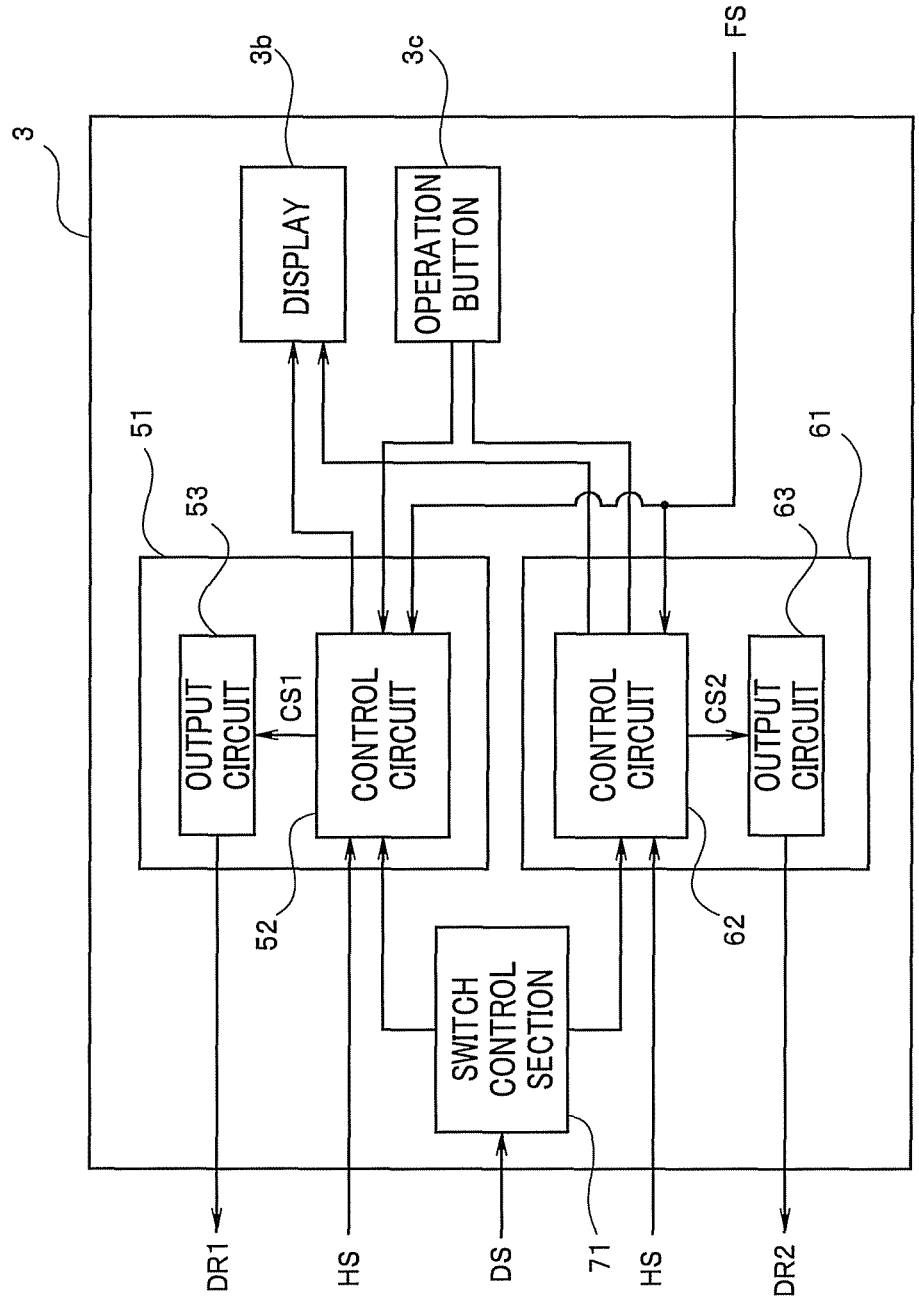
FIG. 22 is a block diagram showing a configuration of a main body apparatus 3.

Next, a configuration of the main body apparatus 3 which is a control unit which controls the output of the aforementioned handpiece 2 will be described. FIG. 22 is a block diagram showing the configuration of the main body apparatus 3. The main body apparatus 3 is the control unit which controls output of the drive signal for supplying at least one of an ultrasound vibration and a high-frequency current to the first device 11.

As shown in FIG. 22, the main body apparatus 3 has an ultrasound output control section 51, a high-frequency output control section 61, and a switch control section 71. The ultrasound output control section 51 includes a control circuit 52 and an output circuit 53 which outputs a drive signal for ultrasound vibration. The high-frequency output control section 61 includes a control circuit 62, and an output circuit 63 which outputs a drive signal for high-frequency current output. The control circuits 52 and 62 are configured by various circuits of a CPU, a memory and the like.

The control circuits 52 and 62 are connected to the display 3b and the operation button 3c of the main body apparatus 3. The operation signal FS from the foot switch 4 and the operation signals HS of the switches 36 and 37 of the handpiece 2 are inputted in the control circuits 52 and 62. The switch control section 71 as the switch control means receives a connection signal DS. The switch control section 71 supplies an output control signal to the control circuits 52 and 62 based on the connection signal DS. As described above, when the second device 12 is connected to the first device 11, the armatures 117a and 201a are brought into contact with each other. By the contact, the main body apparatus 3 can detect that the second device 12 is connected to the first device 11 as the connection signal DS through the signal line 2ab. Accordingly, the armature 117a and the signal line 2ab configure the connection signal output section which can output the connection signal DS which indicates that the second device 12 is connected to the first device 11.

The output circuit 53 supplies a drive signal DR1 for ultrasound vibration to the first device 11. The output circuit 63 supplies a drive signal DR2 for high-frequency current output to the first device 11. The control circuits 52 and 62 respectively supply output control signals CS1 and CS2 to the output circuits 53 and 63 based on setting in the operation button 3c and the operation signals from the foot switch 4 and the switches 36 and 37, and the output circuits 53 and 63 respectively output the drive signals DR1 and DR2 based on the output control signals CS1 and CS2.

The main body apparatus 3 outputs a drive signal for performing ultrasound output, high-frequency output or simultaneous output of ultrasound and high frequency to the handpiece 2 or the first device 11, in accordance with the setting and the operation signal.

As described above, when only the first device 11 is connected, the main body apparatus 3 has three modes that are the ultrasound output mode, the high-frequency output mode and the simultaneous output mode of ultrasound and high frequency. Further, in the case of the handpiece 2 with the first device 11 fitted in the second device 12, the main body apparatus 3 has three modes that are an ultrasound output mode, a high-frequency output mode of bipolar output, and a simultaneous output mode of ultrasound and high frequency of bipolar output (or may be monopolar output).

The main body apparatus 3 controls output of a drive signal for supplying at least one of an ultrasound vibration and a high-frequency current to the first device 11 based on the connection signal DS.

More specifically, when the main body apparatus 3 detects that the first device 11 is connected to the recessed portion 41 which is the attaching and detaching portion of the second device based on the connection signal DS during a surgical operation, for example, the main body apparatus 3 controls output of the drive signal DR2 so as to switch output to bipolar output (or monopolar output) at the time of output of a high-frequency current, and controls output of the drive signal DR1 so as to switch output to ultrasound drive output suitable for treatment by the scissors-shaped treatment portion at the time of output of an ultrasound vibration.

Further, when the main body apparatus 3 detects that the first device 11 is detached from the recessed portion 41 of the second device based on the connection signal DS, the main body apparatus 3 controls the output of the drive signal DR2 so as to switch the output to monopolar output at the time of output of a high-frequency current, and controls the output of the drive signal DR1 so as to switch the output to the ultrasound drive output suitable for treatment by the spatulate treatment portion at the time of output of an ultrasound vibration.

Further, similarly, when the main body apparatus 3 detects that the first device 11 is connected to the recessed portion 41 of the second device 12 based on the connection signal DS, the main body apparatus 3 controls output of the drive signals DR1 and DR2 so as to switch the output to the simultaneous output of an ultrasound vibration and a high-frequency current of bipolar output (or monopolar output) suitable for the treatment by the scissors-shaped treatment portion at the time of simultaneous output of an ultrasound vibration and a high-frequency current.

Furthermore, when the main body apparatus 3 detects that the first device 11 is disengaged from the recessed portion 41 of the second device 12 based on the connection signal DS, the main body apparatus 3 controls output of the drive signals DR1 and DR2 so as to switch the output to the aforesaid ultrasound vibration output of ultrasound drive output suitable for the treatment by the spatulate treatment portion, the aforesaid high-frequency current output of monopolar output, or simultaneous output of an ultrasound vibration and a high-frequency current of monopolar output suitable for the treatment by the spatulate treatment portion.

As above, the main body apparatus 3 can automatically control the output of the drive signal for supplying at least one of an ultrasound vibration and a high-frequency current to the first device 11 based on the connection signal DS.

In the aforementioned embodiment, based on the connection signal DS, the main body apparatus 3 automatically performs change of the output, for example, change of bipolar and monopolar, change of the output value of ultrasound output, or the like, but the main body apparatus 3 may inform a surgeon of the connection situation of the first device 11 and the second device 12 by lighting a predetermined lamp or the like based on the connection signal DS, and the surgeon may perform switch of the output in the operation button or the like of the main body apparatus 3.

Further, the handpiece 2 according to the aforementioned embodiment can individually or simultaneously output both high-frequency output and ultrasound output, but the output switch control of the present embodiment also can be applied to the handpiece capable of only high-frequency output or the handpiece capable of only ultrasound output. For example, in the case of the handpiece capable of only high-frequency output, the main body apparatus 3 makes high-frequency output monopolar output in the case of only the first device, and switch the output so as to make high-frequency output bipolar output when the first device is connected to the second device, based on the connection signal DS. Further in the case of the handpiece capable of performing only ultrasound output, the main body apparatus 3 outputs ultrasound output in the first set value suitable for the spatulate treatment portion in the case of only the first device, and switches the output to output ultrasound output in the second set value suitable for the scissors-shaped treatment portion when the first device is coupled to the second device, based on the connection signal DS.

As above, according to the aforementioned embodiment, the medical apparatus and the surgical treatment instrument can be realized, which are capable of easily changing the surgical treatment instrument of the type for performing treatment by holding living tissue, and the surgical treatment instrument of the type for performing treatment by being brought into contact with living tissue in one treatment instrument.

As the time relating to change of the treatment instrument during a surgical operation is shorter, it is more desirable since the burden on a patient is reduced. The series of operations described above of a surgeon giving an instruction to a nurse or the like and handing the treatment instrument which has been used so far to the nurse or the like, and the nurse or the like performing removal or the like of the treatment instrument from the control apparatus and handing the treatment instrument to be used next to the surgeon, which is performed conventionally, has the problem of being complicated and requiring much time.

Further, the high-frequency treatment instrument proposed in the above described Japanese Patent Application Laid-Open Publication No. 2009-78155 is the forceps having the structure in which the extended portion of the monopolar element is provided at the distal end portion of one of the two members of the bipolar forceps. According to the high-frequency treatment instrument, there is no need of preparing the monopolar treatment instrument and the bipolar treatment instrument respectively, and the surgeon can perform treatment by monopolar output and bipolar output with one treatment instrument.

However, since the high-frequency treatment instrument according to the proposal has the structure for making the monopolar element extendable in one of the two members in the distal end portion of the bipolar forceps, there arise the problems that the one member is increased in size and is complicated, and limitation occurs in the size and shape of the monopolar element. Increase in size and complication of the distal end portion and limitation of the size and the like of the monopolar element lead to degradation of usability of the treatment instrument for a surgeon, and due to increase in size of the distal end portion and limitation of the size and the like of the monopolar element, the field of view of a surgeon is likely to be worsened under observation of laparoscope.

In contrast with this, according to the embodiment of the present invention described above, the medical apparatus and the surgical treatment instrument can be realized, which are capable of easily changing the surgical treatment instrument of the type for performing treatment by holding living tissue, and the surgical treatment instrument of the type for performing treatment by being brought into contact with living tissue in one treatment instrument.

The present invention is not limited to the aforementioned embodiment, and various changes, modifications and the like can be made within the range without changing the gist of the present invention.

What is claimed is:

1. A medical apparatus comprising:
a main body apparatus configured to be switched among a first mode in which ultrasound vibration is outputted, a second mode in which a high-frequency current is outputted, and a third mode in which the ultrasound vibration and the high-frequency current are simultaneously outputted;
a probe comprising a first treatment portion for performing a first treatment on a living tissue, wherein the first treatment portion is formed at a distal end portion of the probe, and is configured to transmit at least one of the ultrasound vibration and the high-frequency current to the living tissue,
a first grasping portion connected to the probe and the main body apparatus, wherein the first grasping portion is configured to be grasped by a user when performing the first treatment;
a first attaching and detaching portion arranged with the first grasping portion, the first attaching and detaching portion comprising a first electric armature;
an insertion portion comprising:
an insertion channel in which the probe is insertable; and
a second treatment portion configured to perform a second treatment, with the living tissue held between the first treatment portion and the second treatment portion when the probe is inserted in the insertion channel; and
an operation portion main body configured to support the insertion portion, wherein the operation portion main body comprises:
a second attaching and detaching portion comprising a second electric armature configured to be detachably connected to the first electric armature when the probe is inserted in the insertion portion; and
a second grasping portion configured to be grasped by the user when performing the second treatment, wherein the second grasping portion comprises a movable handle for opening and closing the second treatment portion with respect to the first treatment portion, wherein the main body apparatus comprises a switch control section configured to perform control for enabling a bipolar output of the high frequency current from the main body apparatus when the first electric armature of the first attaching and detaching portion is connected to the second electric armature of the second attaching and detaching portion and it is detected that the main body apparatus is switched to either the second mode or the third mode, and perform control for enabling a monopolar output of the high frequency current from the main body apparatus when the first electric armature of the first attaching and detaching portion is not connected to the second electric armature of the second attaching and detaching portion and it is detected that the main body apparatus is switched to either the first mode or the third mode.

2. The medical apparatus according to claim 1, further comprising a connection signal output portion configured to detect an electrical conductive state between the first electric armature and the second electric armature and output a connection signal indicating whether or not the first attaching and detaching portion is connected to the second attaching and detaching portion based on the detected electrical conductive state.

3. The medical apparatus according to claim 2, wherein the switch control section is configured to perform control for making a set value related to output of the ultrasound vibration different between when the switch control section detects that the first attaching and detaching portion is connected to the second attaching and detaching portion based on the connection signal and when the switch control section detects that the first attaching and detaching portion is not connected to the second attaching and detaching portion based on the connection signal.

4. The medical apparatus according to claim 1, wherein the connection signal output portion is a signal line connected to the second electric armature.

5. The medical apparatus according to claim 1, wherein the second treatment portion comprises a return line of the high-frequency current.

6. The medical apparatus according to claim 1, wherein
the first treatment portion has a spatulate shape, and
the first treatment portion has a shape of a substantially isosceles triangle at an opposite side from the second treatment portion, in a direction orthogonal to an axis of the probe.

7. The medical apparatus according to claim 1, wherein:
the first treatment portion has a hook shape, and
the first treatment portion has a protruding portion at a predetermined angle at an inner side of the hook shape in a direction orthogonal to an axis of the probe.

8. The medical apparatus according to claim 7, wherein the predetermined angle is in a range of 45 degrees to 100 degrees.

9. A medical apparatus comprising:
an output apparatus configured to output at least an ultrasound signal;
a first device connected to the output apparatus via a cable; and
a second device attachable to and detachable from the first device, wherein the first device comprises:
an ultrasound transducer configured to convert the ultrasound signal outputted by the output apparatus to ultrasound vibration;
a probe comprising a first treatment portion for performing a first treatment on a living tissue, wherein the first treatment portion is formed at a distal end portion of the first device, and is configured to transmit the ultrasound vibration generated by the ultrasound transducer to the living tissue;
a first grasping portion configured to store the ultrasound transducer, and to be grasped by a user when performing the first treatment; and
a first attaching and detaching portion comprising a first armature, wherein the second device comprises:
an insertion portion comprising:
an insertion channel in which the probe is insertable; and
a second treatment portion configured to perform a second treatment with the living tissue held between the first treatment portion and the second treatment portion when the probe is inserted in the insertion channel;
a second grasping portion configured to be grasped by the user when performing the second treatment, wherein the second grasping portion comprises a movable handle for opening and closing the second treatment portion with respect to the first treatment portion to releasably hold the living tissue between the first treatment portion and the second treatment portion; and
a second attaching and detaching portion comprising a second armature configured to be detachably connected to the first armature of the first device when the probe is inserted in the insertion channel, wherein the output apparatus comprises:
an ultrasound output control section configured to control output of the ultrasound signal to the ultrasound transducer; and
a switch control section configured to:
detect whether or not the first armature of the first device is connected to the second armature of the second device,
control the ultrasound output control section to output to the ultrasound transducer the ultrasound control signal, the ultrasound control signal corresponding to a first set value, when it is detected that the first armature is not connected to the second armature, and
control the ultrasound output control section to output to the ultrasound transducer the ultrasound control signal, the ultrasound control signal corresponding to a second set value different from the first set value, when it is detected that the first armature is connected to the second armature.

10. A medical apparatus comprising:
an output apparatus configured to output at least a high-frequency signal;
a first device connected to the output apparatus via a cable; and
a second device attachable to and detachable from the first device, wherein the first device comprises:
a probe comprising a first treatment portion for performing a first treatment on a living tissue, wherein the first treatment portion is formed at a distal end portion of the first device, and is configured to transmit a high-frequency current to the living tissue based on the high-frequency signal outputted by the output apparatus;
a first grasping portion configured to be grasped by a user when performing the first treatment; and
a first attaching and detaching portion comprising a first armature,
wherein the second device comprises:
an insertion portion comprising:
an insertion channel in which the probe is insertable;
a second treatment portion; and
a return line of the high-frequency current,
wherein the insertion portion is configured to perform a second treatment on the living tissue, with the living tissue held between the first treatment portion and the second treatment portion when the probe is inserted in the insertion channel;
a second grasping portion configured to be grasped by the user when performing the second treatment, wherein the second grasping portion comprises a movable handle for opening and closing the second treatment portion with respect to the first treatment portion to releasably hold the living tissue between the first treatment portion and the second treatment portion; and
a second attaching and detaching portion comprising a second armature configured to be detachably connected to the first armature of the first device when the probe is inserted in the insertion channel,
wherein the output apparatus comprises:
a high-frequency output control section configured to control output of the high-frequency signal; and
a switch control section configured to:
detect whether or not the first armature of the first device is connected to the second armature of the second device,
control the high-frequency output control section to output a monopolar output of the high-frequency current when it is detected that the first armature is not connected to the second armature, and
control the high-frequency output control section so as to output a bipolar output of the high-frequency current when it is detected that the first armature is connected to the second armature.

* * * * *